United States Patent
Zheng et al.

(10) Patent No.: US 12,085,564 B2
(45) Date of Patent: Sep. 10, 2024

(54) ASSAY TO DETERMINE IN VIVO RECEPTOR OCCUPANCY

(71) Applicant: BRISTOL-MYERS SQUIBB COMPANY, Princeton, NJ (US)

(72) Inventors: Naiyu Zheng, Princeton, NJ (US); Ian MacQuarie Catlett, Pennington, NJ (US); Jianing Zeng, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 944 days.

(21) Appl. No.: 17/051,466

(22) PCT Filed: May 9, 2019

(86) PCT No.: PCT/US2019/031524
§ 371 (c)(1),
(2) Date: Oct. 29, 2020

(87) PCT Pub. No.: WO2019/217684
PCT Pub. Date: Nov. 14, 2019

(65) Prior Publication Data
US 2021/0156854 A1     May 27, 2021

Related U.S. Application Data

(60) Provisional application No. 62/669,442, filed on May 10, 2018.

(51) Int. Cl.
*G01N 33/68* (2006.01)
*G01N 30/02* (2006.01)
*G01N 33/543* (2006.01)

(52) U.S. Cl.
CPC ... *G01N 33/54393* (2013.01); *G01N 33/6851* (2013.01); *G01N 2030/027* (2013.01)

(58) Field of Classification Search
CPC ......... G01N 33/54393; G01N 33/6851; G01N 2030/027; G01N 2333/912; G01N 33/543; G01N 33/68; C12Y 207/10001
See application file for complete search history.

(56) References Cited

U.S. PATENT DOCUMENTS

2009/0062255 A1   3/2009   Gourdeau et al.
2016/0252509 A1   9/2016   Cravatt et al.

FOREIGN PATENT DOCUMENTS

WO    WO-2012010240 A1   1/2012
WO       2016100593 A1   6/2016
(Continued)

OTHER PUBLICATIONS

Lanshoeft et al. (Generic Hybrid Ligand Binding Assay Liquid Chromatography High-Resolution Mass Spectrometry-Based Workflow for Multiplexed Human Immunoglobulin G1 Quantification at the Intact Protein Level: Application to Preclinical Pharmacokinetic Studies, Anal. Chem. 2017, 89, 4, 2628-2635) (Year: 2017).*

(Continued)

*Primary Examiner* — Ann Montgomery
*Assistant Examiner* — Chau N. B. Tran
(74) *Attorney, Agent, or Firm* — Sterne, Kessler, Goldstein & Fox P.L.L.C.

(57) ABSTRACT

The present invention relates to assays for monitoring and measuring the binding of a drug of interest to a receptor. In this assay, a blood sample collected from a subject dosed with the compound of interest is incubated with a lysis solution containing a quencher. The drug bound and quencher bound receptor is then isolated from the lysed blood sample. The isolated drug bound and quencher bound receptor is digested to generate surrogate drug bound and quencher bound peptides. The amount of surrogate peptides is determined. Receptor occupancy can be determined by comparing the amount of drug bound surrogate peptide to (Continued)

the total of drug bound and quencher bound surrogate peptide.

17 Claims, 14 Drawing Sheets

Specification includes a Sequence Listing.

(56) References Cited

FOREIGN PATENT DOCUMENTS

WO  WO-2016100593 A1 *  6/2016
WO  WO-2019217684 A1    11/2019

OTHER PUBLICATIONS

Neubert et al.(Quantification of biotherapeutic targets: new opportunities with immunoaffinity LC-MS/MS, 2014—IDS#12). (Year: 2017).*
Brahmer, J. R., et al., The New England Journal of Medicine 2012, 366, 2455-2465.
Arrowsmith, J., Nature Reviews. Drug Discovery 2011, 10, 87.
Barf, T., et.al., The Journal of pharmacology and experimental therapeutics 2017.
E. K. Evans et al : "Inhi bi ti on of Btk with CC-292 Provi des Earl y Pharmacodynami c Assessment of Acti vi ty i n Mi ce and Humans",Journal of Pharmacology and Experim Ental Therapeutics.
Fung, E.N et al., Bioanalysis 2016, 8, 847-856.
Honigberg, L. A; J. Proceedings of the National Academy of Sciences of the United States of America 2010, 107, 13075-13080.
Hua, F., et al., Journal of Clinical Pharmacology 2014, 54, 14-22.
Kola, I., et al., J. Nature Reviews. Drug Discovery 2004, 3, 711-715.
Liang, M, et al., Cytometry B Clin Cytom 2016, 90, 117-127.
Morgan, P., et al., Drug Discovery Today 2012, 17, 419- 424.
Nai Yu Zheng et al : "Determi nati on of Real Time i n Vi vo Drug Receptor Occupancy for a Coval ent Bi ndi ng Drug as a Cl i ni calPharmacodynami c Bi omarker by Immunocapture—LC-MS/MS",Analyti Cal Chemi Stry, vol. 91, No. 13, Jun. 5, 2019 (Jun. 5, 2019).
Neubert, H., et. al., Bioanalysis 2014, 6, 1731-1733.
Rutgeerts, P. J., et.al., Gut 2013, 62, 1122-1130.
Seiler, T., et. al., Expert Opin Investig Drugs 2017, 26, 909-915.
Stevenson, L., et. al., Bioanalysis 2013, 5, 2903-2918.
Tolcher, A W., et. al., Journal of Clinical Oncology : Official Journal of the American Society of Clinical Oncology 2009, 27, 5800-5807.
Topalian, S. L., et. al., The New England Journal of Medicine 2012, 366, 2443-2454.
Whang, J. A, et. al., Drug Discovery Today 2014, 19, 1200-1204.
Woska, J. R., Jr., et. al., Journal of immunological methods 2003, 277, 101-115.
Jianing Zeng: "An LC-MS Receptor Occupancy assay for Dose Selection in FIH", AAPS PHARMSCI360, Nov. 7, 2008.
Jesudason, Ph.D., C., et al., "In Vivo Receptor Occupancy in Rodents by LC-MS/MS," in The Assay Guidance Manual, accessed at https://www.ncbi.nlm.nih.gov/sites/books/NBK424998/, 8 pages, Markossian, S., eds., Eli Lilly & Company and the National Center for Advancing Translational Sciences, Bethesda, MD, United States (Mar. 2017).
Li, R., et al., "Determination of Batefiban concentration in rhesus monkey plasma by LC-MS/MS and pharmacokinetic studies," Chinese Journal of New Drugs 15:1798-1802, Chinese Medical Science Press, China (Dec. 2012).
Lutz, J.D., et al., "A Pharmacokinetic-Pharmacodynamic (PKPD) Model Describing Irreversible Inhibition of Bruton's Tyrosine Kinase by GS-4059," Poster presentation at the 2016 ACR/ARHP Annual Meeting in Foster City, CA, United States (Sep. 28, 2016).
PhRMA Report, "Biopharmaceutical Research & Development: The Process Behind New Medicines," 24 pages, PhRMA, United States (May 2015).
International Search Report and Written Opinion for International Application No. PCT/US2019/031524, European Patent Office, Netherlands, mailed on Jul. 23, 2019, 13 pages.

* cited by examiner

FIG. 2

```
SP|Q06187|BTK_HUMAN     MAAVILESIFLKRSQQKKKTSPLNFKKRLFLLTVHKLSYYEYDFERGRRGSKKGSIDVEK 60
TR|F6V0I6|F6V0I6_MACMU  MAAVILESIFLKRSQQKKKTSPLNFKKRLFLLTVHKLSYYEYDFERGRRGSKKGSIDVEK 60
                        ************************************************************

SP|Q06187|BTK_HUMAN     ITCVETVVPEKNPPPERQIPRRGEESSEMEQISIIERFPYPFQVVYDEGPLYVFSPTEEL 120
TR|F6V0I6|F6V0I6_MACMU  ITCVETVVPEKNPPPERQIPRRGEESSEMEQISIIERFPYPFQVVYDEGPLYVFSPTEEL 120
                        ************************************************************

SP|Q06187|BTK_HUMAN     RKRWIHQLKNVIRYNSDLVQKYHPCFWIDGQYLCCSQTAKNAMGCQILENRNGSLKPGSS 180
TR|F6V0I6|F6V0I6_MACMU  RKRWIHQLKNVIRYNSDLVQKYHPCFWIDGQYLCCSQTAKNAMGCQILENRNGSLKPGSS 180
                        ************************************************************

SP|Q06187|BTK_HUMAN     HRKTKKPLPPTPEEDQILKKPLPPEPAAAPVSTSELKKVVALYDYMPMNANDLQLRKGDE 240
TR|F6V0I6|F6V0I6_MACMU  HRKTKKPLPPTPEEDQILKKPLPPEPAAAPVSTSELKKVVALYDYMPMNANDLQLRKGDE 240
                        ************************************************************

SP|Q06187|BTK_HUMAN     YFILEESNLPWWRARDKNGQEGYIPSNYVTEAEDSIEMYEWYSKHMTRSQAEQLLKQEGK 300
TR|F6V0I6|F6V0I6_MACMU  YFILEESNLPWWRARDKNGQEGYIPSNYVTEAEDSIEMYEWYSKHMTRSQAEQLLKQEGK 300
                        ************************************************************

SP|Q06187|BTK_HUMAN     EGGFIVRDSSKAGKYTVSVFAKSTGDPQGVIRHYVVCSTPQSQYYLAEKHLFSTIPELIN 360
TR|F6V0I6|F6V0I6_MACMU  EGGFIVRDSSKAGKYTVSVFAKSTGDPQGVIRHYVVCSTPQSQYYLAEKHLFSTIPELIN 360
                        ************************************************************

SP|Q06187|BTK_HUMAN     YHQHNSAGLISRLKYPVSQQNKNAPSTAGLGYGSWEIDPKDLTFLKELGTGQFGVVKYGK 420
TR|F6V0I6|F6V0I6_MACMU  YHQHNSAGLISRLKYPVSQQNKNAPSTAGLGYGSWEIDPKDLTFLKELGTGQFGVVKYGK 420
                        ************************************************************

SP|Q06187|BTK_HUMAN     WRGQYDVAIKMIKEGSMSEDEFIEEAKVMMNLSHEKLVQLYGVCTKQRPIFIITEYMANG 480
TR|F6V0I6|F6V0I6_MACMU  WRGQYDVAIKMIKEGSMSEDEFIEEAKVMMNLSHEKLVQLYGVCTKQRPIFIITEYMANG 480
                        ************************************************************

SP|Q06187|BTK_HUMAN     CLLNYLREMRHRFQTQQLLEMCKDVCEAMEYLESKQFLHRDLAARNCLVNDQGVVKVSDF 540
TR|F6V0I6|F6V0I6_MACMU  CLLNYLREMRHRFQTQQLLEMCKDVCEAMEYLESKQFLHRDLAARNCLVNDQGVVKVSDF 540
                        ************************************************************

SP|Q06187|BTK_HUMAN     GLSRYVLDDEYTSSVGSKFPVRWSPPEVLMYSKFSSKSDIWAFGVLMWEIYSLGKMPYER 600
TR|F6V0I6|F6V0I6_MACMU  GLSRYVLDDEYTSSVGSKFPVRWSPPEVLMYSKFSSKSDIWAFGVLMWEIYSLGKMPYER 600
                        ************************************************************

SP|Q06187|BTK_HUMAN     FTNSETAEHIAQGLRLYRPHLASEKVYTIMYSCWHEKADERPTFKILLSNILDVMDEES  659
TR|F6V0I6|F6V0I6_MACMU  FTNSETAEHIAQGLRLYRPHLASEKVYTIMYSCWHEKADERPTFKILLSNILDVMDEES  659
                        ************************************************************
```

Control Blank

LLOQ (0.250 nM)

Internal Standard

SEQUENCE LISTING

```
<160> NUMBER OF SEQ ID NOS: 10

<210> SEQ ID NO 1
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Cys at position 15 is the binding site of an
      irreversible quencher or compound of interest

<400> SEQUENCE: 1

Gln Arg Pro Ile Phe Ile Ile Thr Glu Tyr Met Ala Asn Gly Cys Leu
1               5                   10                  15

Leu Asn Tyr Leu Arg
            20

<210> SEQ ID NO 2
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Cys at position 5 is the binding site of an
      irreversible quencher or compound of interest

<400> SEQUENCE: 2

Met Ala Asn Gly Cys Leu Leu Asn Tyr
1               5

<210> SEQ ID NO 3
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: Cys at position 6 is the binding site of an
      irreversible quencher or compound of interest

<400> SEQUENCE: 3

Tyr Met Ala Asn Gly Cys Leu Leu Asn Tyr Leu Arg Glu
1               5                   10

<210> SEQ ID NO 4
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: Cys at position 15 is the binding site of an
      irreversible quencher or compound of interest

<400> SEQUENCE: 4

Gln Arg Pro Ile Phe Ile Ile Thr Glu Tyr Met Ala Asn Gly Cys Leu
1               5                   10                  15

Leu Asn Tyr Leu Arg Glu Met Arg His Arg Phe Gln Thr Gln Gln Leu
            20                  25                  30

Leu Glu Met Cys Lys
            35

<210> SEQ ID NO 5
<211> LENGTH: 37
<212> TYPE: PRT
```

```
<213> ORGANISM: Homo sapiens
<220> FEATURE:
<221> NAME/KEY: PEPTIDE
<222> LOCATION: (1)..(37)
<223> OTHER INFORMATION: Cys at position 16 is the binding site of an
      irreversible quencher or compound of interest

<400> SEQUENCE: 5

Lys Gln Arg Pro Ile Phe Ile Ile Thr Glu Tyr Met Ala Asn Gly Cys
1               5                   10                  15

Leu Leu Asn Tyr Leu Arg Glu Met Arg His Arg Phe Gln Thr Gln Gln
            20                  25                  30

Leu Leu Glu Met Cys
        35

<210> SEQ ID NO 6
<211> LENGTH: 64
<212> TYPE: PRT
<213> ORGANISM: Homo sapiens
<220> FEATURE:
<221> NAME/KEY: PEPTIDE
<222> LOCATION: (1)..(64)
<223> OTHER INFORMATION: Cys at position 42 is the binding site of an
      irreversible quencher or compound of interest

<400> SEQUENCE: 6

Asp Glu Phe Ile Glu Glu Ala Lys Val Met Met Asn Leu Ser His Glu
1               5                   10                  15

Lys Leu Val Gln Leu Tyr Gly Val Cys Thr Lys Gln Arg Pro Ile Phe
            20                  25                  30

Ile Ile Thr Glu Tyr Met Ala Asn Gly Cys Leu Leu Asn Tyr Leu Arg
        35                  40                  45

Glu Met Arg His Arg Phe Gln Thr Gln Gln Leu Leu Glu Met Cys Lys
    50                  55                  60

<210> SEQ ID NO 7
<211> LENGTH: 65
<212> TYPE: PRT
<213> ORGANISM: Homo sapiens
<220> FEATURE:
<221> NAME/KEY: PEPTIDE
<222> LOCATION: (1)..(65)
<223> OTHER INFORMATION: Cys at position 59 is the binding site of an
      irreversible quencher or compound of interest

<400> SEQUENCE: 7

Gly Gln Tyr Asp Val Ala Ile Lys Met Ile Lys Glu Gly Ser Met Ser
1               5                   10                  15

Glu Asp Glu Phe Ile Glu Glu Ala Lys Val Met Met Asn Leu Ser His
            20                  25                  30

Glu Lys Leu Val Gln Leu Tyr Gly Val Cys Thr Lys Gln Arg Pro Ile
        35                  40                  45

Phe Ile Ile Thr Glu Tyr Met Ala Asn Gly Cys Leu Leu Asn Tyr Leu
    50                  55                  60

Arg
65

<210> SEQ ID NO 8
<211> LENGTH: 25
<212> TYPE: PRT
<213> ORGANISM: Artificial Sequence
<220> FEATURE:
<223> OTHER INFORMATION: Phe at position 7 is [13C9,15N]-phenylalanine;
      Cys at position 17 is the binding site of an irreversible quencher
```

-continued

<400> SEQUENCE: 8

Thr Arg Gln Arg Pro Ile Phe Ile Ile Thr Glu Tyr Met Ala Asn Gly
1               5                   10                  15

Cys Leu Leu Asn Tyr Leu Arg Glu Ala
            20                  25

<210> SEQ ID NO 9
<211> LENGTH: 659
<212> TYPE: PRT
<213> ORGANISM: Homo sapiens

<400> SEQUENCE: 9

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

```
Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
            405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
            435                 440                 445

Met Met Asn Leu Ser His Glu Lys Leu Val Gln Leu Tyr Gly Val Cys
        450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
            485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
            515                 520                 525

Val Asn Asp Gln Gly Val Val Lys Val Ser Asp Phe Gly Leu Ser Arg
        530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
            565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
            595                 600                 605

His Ile Ala Gln Gly Leu Arg Leu Tyr Arg Pro His Leu Ala Ser Glu
        610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
            645                 650                 655

Glu Glu Ser

<210> SEQ ID NO 10
<211> LENGTH: 659
<212> TYPE: PRT
<213> ORGANISM: Rhesus cytomegalovirus

<400> SEQUENCE: 10

Met Ala Ala Val Ile Leu Glu Ser Ile Phe Leu Lys Arg Ser Gln Gln
1               5                   10                  15

Lys Lys Lys Thr Ser Pro Leu Asn Phe Lys Arg Leu Phe Leu Leu
            20                  25                  30

Thr Val His Lys Leu Ser Tyr Tyr Glu Tyr Asp Phe Glu Arg Gly Arg
        35                  40                  45
```

```
Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
            115                 120                 125

Lys Asn Val Ile Arg Tyr Asn Ser Asp Leu Val Gln Lys Tyr His Pro
        130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
                180                 185                 190

Glu Glu Asp Gln Ile Leu Lys Lys Pro Leu Pro Pro Glu Pro Ala Ala
            195                 200                 205

Ala Pro Val Ser Thr Ser Glu Leu Lys Lys Val Val Ala Leu Tyr Asp
        210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
                260                 265                 270

Glu Asp Ser Ile Glu Met Tyr Glu Trp Tyr Ser Lys His Met Thr Arg
            275                 280                 285

Ser Gln Ala Glu Gln Leu Leu Lys Gln Glu Gly Lys Glu Gly Gly Phe
        290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430
```

```
Lys Glu Gly Ser Met Ser Glu Asp Glu Phe Ile Glu Glu Ala Lys Val
            435                 440                 445

Met Met Asn Leu Ser His Glu Lys Leu Val Gln Leu Tyr Gly Val Cys
        450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
            515                 520                 525

Val Asn Asp Gln Gly Val Val Lys Val Ser Asp Phe Gly Leu Ser Arg
            530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
                580                 585                 590

Leu Gly Lys Met Pro Tyr Glu Arg Phe Thr Asn Ser Glu Thr Ala Glu
            595                 600                 605

His Ile Ala Gln Gly Leu Arg Leu Tyr Arg Pro His Leu Ala Ser Glu
        610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser
```

ASSAY TO DETERMINE IN VIVO RECEPTOR OCCUPANCY

CROSS REFERENCE TO RELATED APPLICATIONS

This application is a national phase application under 35 U.S.C. § 371 of International Application No. PCT/US2019/031524 filed on May 9, 2019, which claims the priority benefit of U.S. Provisional Application 62/669,442, filed May 10, 2018; each of which is incorporated herein by reference in its entirety.

FIELD OF THE INVENTION

The present invention relates to methods to directly measure real time in vivo receptor occupancy by a covalently bound compound in blood lysate. More specifically, the present invention relates to real time in vivo BTK receptor occupancy measurement as a pharmacodynamics biomarker for clinical drug development.

BACKGROUND OF THE INVENTION

Drug discovery and development is a long and high risk process. The average cost of developing a successful new medicine has been estimated to be as much as $2.6 billion due to the failure of countless drug candidates during the early discovery and development process, and the overall survival rate of the drug candidate entering the clinical studies is estimated to be less than 12% (PhRMA Report, "Biopharmaceutical Research & Development: The Process Behind New Medicines", 2015). The major issues causing the failure of these drug candidates were related to insufficient or lacking clinical efficacy during the late development phase, particularly during the proof of concept (phase II) clinical trials (Kola, I., et. al., J. Nature Reviews. Drug Discovery 2004, 3, 711-715; Arrowsmith, J., Nature Reviews. Drug Discovery 2011, 10, 87; Morgan, P., et. al., Drug Discovery Today 2012, 17, 419-424).

Many small molecule drugs and biologics under development have been designed to mediate the immune system. As such, these drug candidates often require very low dose levels to trigger the desired response. Therefore, early understanding of the pharmacokinetic (PK) and pharmacodynamic (PD) properties of these drug candidates is crucial to determine the appropriate dose range for clinical trials (Topalian, S. L., et. al., The New England Journal of Medicine 2012, 366, 2443-2454; Brahmer, J. R., et. al., The New England Journal of Medicine 2012, 366, 2455-2465; Tolcher, A. W., et. al., Journal of Clinical Oncology: Official Journal of the American Society of Clinical Oncology 2009, 27, 5800-5807; Hua, F., et. al., Journal of Clinical Pharmacology 2014, 54, 14-22; Rutgeerts, P. J., et. al., Gut 2013, 62, 1122-1130). To improve the clinical efficiency and reduce costs during the drug development phase, quantitative measurement of PD profile is as important as the PK profile for the rational design of clinical trials. This is especially true where the PD profile changes with multiple doses.

Receptor occupancy (RO) assays measure the binding of a molecule to its receptor protein (or target) and provide quantitative data that can be used to generate a PD profile (Liang, M., et. al., Cytometry B Clin Cytom 2016, 90, 117-127). The measurement of RO is a critical determination for relating efficacy to mechanism in preclinical animal models and in clinical studies. In practice, RO is particularly useful in making dose escalation decisions in the first in human (FIH) study.

Bruton's tyrosine kinase (BTK) plays a key role in the signal transduction and activation via B-cell receptor, Fc receptor- and RANKL pathways (Seiler, T., et. al., Expert Opin Investig Drugs 2017, 26, 909-915; Whang, J. A., et. al., Drug Discovery Today 2014, 19, 1200-1204). For antibody-based drugs, the RO is usually monitored by flow cytometry using antibodies that compete with the target molecule for the measurement of free receptor and non-competing antibodies for the measurement of the total receptor (Liang, M, et. al., Cytometry B Clin Cytom 2016, 90, 117-127; Woska, J. R., Jr., et. al., Journal of immunological methods 2003, 277, 101-115). However, for small molecule antagonist, there are no antibody reagents that exist for the direct detection of occupied receptor by flow cytometry. Previously, BTK RO of ibrutinib in peripheral blood mononuclear cells (PBMCs) was determined by using a fluorescent affinity probe that bound to active occupancy site of free (unoccupied) BTK, followed by detection using SDS/PAGE and fluorescent gel scanning (Honigberg, L. A.; J. Proceedings of the National Academy of Sciences of the United States of America 2010, 107, 13075-13080). The fluorescent affinity probe-based assay can only determine the amount of free BTK, therefore, an additional assay using Western blot is required to measure the total BTK. Due to the large number of samples generated in clinical studies, the use of two assay platforms is not practical. In addition, the method lacks direct comparability between the unbound measurement and total measurement, which results in high assay variation.

Recently, an ELISA based BTK RO assay using a biotinylated covalent probe has been reported and utilized in an acalabrutinib and CC-292 clinical study (Barf, T., et. al., The Journal of pharmacology and experimental therapeutics 2017; Evans, E. K., et. al., The Journal of pharmacology and experimental therapeutics 2013, 346, 219-22). In this approach, only the free BTK is detected while washing away the drug bound BTK (DB-BTK). The total BTK concentration is determined using the pre-dose sample with an assumption that total BTK level remains consistent across samples.

Alternatively, a separate time-resolved fluorescence resonance energy transfer (TR-FRET)-based assay for free and total BTK can be used to estimate the BTK occupancy in peripheral blood mononucleocytes (PBMCs) (Lutz, J. D. N., et. al., Poster presentation at the 7th American Conference on Pharmacometrics (ACoP7) in Bellevue, WA Oct. 23-26, 2016. 2016). However, the free and total BTK are measured independently, rather than simultaneously in the same sample and total BTK levels were found to vary significantly across samples (Honigberg, L. A., supra). Therefore, the ELISA or TR-FRET-based approaches are limited by the inherent variability resulting from the methodological choice.

Liquid chromatography-tandem mass spectrometry (LC-MS/MS) assay has demonstrated potential in protein quantitation due to its excellent assay selectivity and multiplexing capability (Neubert, H., et. al., Bioanalysis 2014, 6, 1731-1733). In particular, the "hybrid" LBA-LC-MS assay that combines immunocapture enrichment, followed by LC-MS/MS detection has become a powerful technology platform to measure protein biomarkers or therapeutics with superb detection selectivity (Stevenson, L., et. al., Bioanalysis 2013, 5, 2903-2918). The major benefit of the LC-MS assay is its ability to quantify both DB-BTK and free BTK simultaneously in the same sample. Therefore the RO determination is much less sensitive to sample or run variation.

However, LC-MS assay development poses a number of challenges. First, blood samples from animals or humans dosed with drug may contain excess amount of drug, which will react with free receptor ex vivo to form drug bound receptor, resulting in the overestimation of RO. Second, LC-MS/MS is usually less sensitive than an ELISA assay.

BRIEF SUMMARY OF THE INVENTION

The present invention relates to assays for monitoring and measuring the binding of a drug of interest to a receptor. In this assay, a blood sample collected from a subject dosed with the compound of interest is incubated with a lysis solution containing a quencher. The drug bound and quencher bound receptor is then isolated from the lysed blood sample. The isolated drug bound and quencher bound receptor is digested to generate surrogate drug bound and quencher bound peptides. The amount of surrogate peptides is determined. Receptor occupancy can be determined by comparing the amount of drug bound surrogate peptide to the total of drug bound and quencher bound surrogate peptide.

In one embodiment of the invention, the compound of interest covalently binds to the receptor.

In another embodiment of the invention, the quencher competes with the compound of interest to irreversibly bind the receptor at the same site as the compound of interest.

In another embodiment of the invention, the quencher is added to the lysis buffer at levels in molar excess of the compound of interest. In another embodiment of the invention, the quencher is added to the lysis buffer in an amount 105 to 1000 fold excess, based on the endogenous receptor concentration.

In another embodiment of the invention, the lysis solution with quencher is added immediately after the blood sample is collected. In another embodiment of the invention, the lysis solution with quencher is added within 5 minutes of the blood sample collection In another embodiment of the invention, the drug bound and quencher bound receptor is isolated using an immunocapture step. In another embodiment of the invention the receptor binds specifically to the capture agent, which is immobilized on a solid support (e.g., magnetic beads, agarose beads or column packing material), and thus is separated from other endogenous proteins and peptides, which do not bind very tightly to the capture antibody [Fung, E. N. et. al., *Bioanalysis* 2016, 8, 847-856].

In another embodiment of the invention, the drug bound and quencher bound receptor is removed from the immunocapture substrate before the digestion step.

In another embodiment of the invention, the drug bound and quencher bound receptor is digested while still associated with the immunocapture substrate.

In another embodiment of the invention, the protease utilized during the digestion step is selected from the group consisting of serine proteases, cysteine proteases, threonine proteases, aspartic proteases, glutamic proteases and metalloproteases. Examples of proteases include, trypsin, chymotrypsin, Glu-C protease, Lys-C protease, Lys-N protease, Asp-N protease, Arg-C protease.

In another embodiment of the invention, the drug bound and quencher bound surrogate peptides are measured simultaneously by a single LC-MS/MS run.

In another embodiment of the invention, receptor occupancy is calculated by comparing the amount of drug bound surrogate peptide to the total amount of drug bound and quencher bound surrogate peptide.

In one embodiment of the invention, receptor occupancy is measured by 1) collecting blood from a subject dosed with a compound of interest that irreversibly binds to the receptor, 2) immediately adding to the collected blood a lysis solution containing a quencher compound that irreversibly binds to the same site as the compound of interest, 3) isolating drug and quencher bound receptor from the lysed and quenched blood sample using an immunocapture step, 4) digesting the isolated drug and quencher bound receptor while still bound to the immunocapture substrate, 5) measuring the amount of drug bound and quencher bound surrogate peptides simultaneously in a single LC-MS/MS run and 6) determining receptor occupancy by comparing the amount of drug bound surrogate peptide to the total amount of drug bound and quencher bound surrogate peptide.

In one preferred aspect of the above embodiments, the receptor is BTK, the compound of interest is shown in FIG. 1A and the corresponding quencher is shown in FIG. 1B.

In another preferred aspect of the above embodiments, the immunocapture substrate is Streptavidin T1 Capture Beads.

In another preferred aspect of the above embodiments, mAb clone #MAB 5807 or mAb clone #MAB D3H5 is the anti-BTK antibody attached to the immunocapture substrate.

In another preferred aspect of the above embodiments, the isolated quencher bound and drug bound BTK is digested with trypsin while still associated with the immunocapture bead.

In another preferred aspect of the above embodiments, BTK receptor occupancy is calculated by comparing the amount of drug bound surrogate peptide to the total of drug bound and quencher bound surrogate peptide.

In one embodiment of the invention, BTK receptor occupancy is measured by 1) collecting blood from a subject dosed with the compound shown in FIG. 1A, 2) immediately adding a lysis solution containing the quencher compound shown in FIG. 1B, 3) isolating drug and quencher bound BTK using an immunocapture step, 4) digesting the isolated drug and quencher bound BTK with trypsin while still associated with the immuocapture bead, 5) measuring the amount of drug bound and quencher bound surrogate peptides simultaneously in a single LC-MS/MS run and 6) determining BTK receptor occupancy by comparing the amount of drug bound surrogate peptide to the total of drug bound and quencher bound surrogate peptide.

BRIEF DESCRIPTION OF THE FIGURES

FIG. 2 shows the sequence alignment of BTK proteins from human and monkey (Rhesus/Cyno), respectively. Boxes indicate tryptic peptides used for analysis. Within the amino acid sequence, Cys 481 (marked by the arrow) is bound to either Compound A (DB-BTK) or the quencher compound (QB-BTK). Tryptic peptide QRPIFIITEYMANGCLLNYLR (SEQ ID NO: 1, as shown in Table 1) bound to either the compound of FIG. 1A or 1B was used for quantitation.

REFERENCE TO SEQUENCE LISTING SUBMITTED ELECTRONICALLY VIA EFS-WEB

Figure 1A:
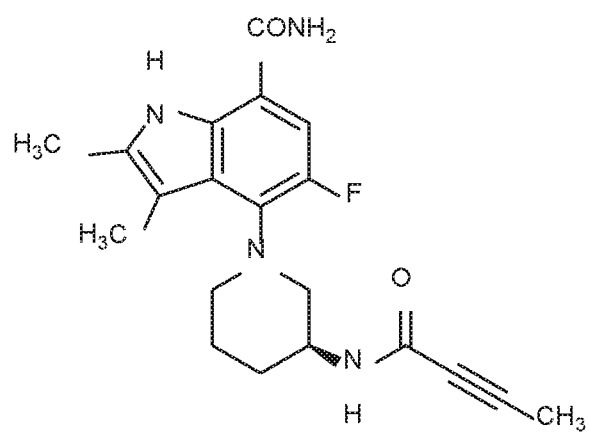
FIGS. 1A and 1B shows the structure of A) Compound A; B) quencher compound.

The content of the electronically submitted sequence listing in ASCII text file 12728WOPCT_ST25.txt (Size: 16 kb, created on Apr. 8, 2019) filed with the application is herein incorporated by reference in its entirety.

DETAILED DESCRIPTION OF THE INVENTION

The present invention may be understood more readily by reference to the following detailed description of the preferred embodiments of the invention and the Examples included herein.

As utilized herein, the term "irreversibly bound" is refers to a type of compound that binds permanently to a receptor, either by forming a covalent bond to the active site, or alternatively just by binding so tightly that the rate of dissociation is effectively zero at relevant time scales.

As utilized herein, the terms "compound of interest" and "drug" are used interchangeably and refer to the molecule binding to the target of interest.

As utilized herein, the terms "target" and "receptor" are used interchangeably when referring to the focus of the RO assay.

As utilized herein, the term "immediately" when referring to when the lysis solution containing the quencher molecule is added to the blood sample means as soon as possible after the blood sample is collected. Alternately, the lysis solution containing the quencher molecule is added within the first 5 minutes after the blood sample is collected.

This invention describes the development of an in vivo receptor occupancy assay, more specifically an in vivo Bruton's tyrosine kinase (BTK) receptor occupancy (RO) assay. Assay sensitivity is key to determine the RO at very high or very low occupancy levels where either the bound or free target could be less than 5%.

The present invention is a method comprising the steps of a) collecting a blood sample from a subject treated with the compound of interest, b) adding a lysis solution containing a receptor specific quencher to the blood sample, c) isolating the receptor of interest, d) digesting the isolated receptor to generate surrogate peptides, e) measuring the amount of surrogate peptides and determining receptor occupancy by comparing the amount of drug bound surrogate peptide to the total amount of drug bound and quencher bound surrogate peptides.

Collecting a Blood Sample from a Subject Administered with the Compound of Interest.

In one embodiment of the invention, the compound of interest irreversibly binds to at least one amino acids of the receptor. An example of a compound of interest is the compound shown in FIG. 1A, which irreversibly binds to BTK.

Lysis Solution Containing a Receptor Specific Quencher is Added to the Blood Sample There were a number of challenges impacting the selectivity and sensitivity of the receptor occupancy (RO) assay development. In particular, the presence of free drug and free receptor in the blood sample could generate drug bound receptor ex vivo during the lysis step, which would lead to an overestimation of RO. It was discovered that addition of a receptor specific quencher during the lysis step rapidly converts the free receptor to quencher bound (QB) receptor, thereby blocking ex vivo drug bound receptor formation.

In one embodiment, the RO assay comprises the lysis of the blood sample in the presence of a quencher to convert endogenous receptor into quencher bound receptor thereby preventing the formation of endogenous drug bound receptor.

In one embodiment of the invention, the quencher irreversibly binds to the same amino acid as the compound of interest. Preferably, the quencher competes with the compound of interest in binding to the receptor. In another embodiment of the invention, the quencher is added to the lysis solution in molar excess to the compound of interest. In another embodiment of the invention, the lysis solution containing the quencher is added immediately after collecting the blood sample.

One skilled in the art would be aware of cell lysis solutions. Commercially available cell lysis buffer solutions include NP-40 lysis buffer (␣ TheromFisher Scientific), RIPA lysis buffer (Abbexa), ACK lysing buffer (TheromFisher Scientific), cell lysis buffer (10×) (Cat No: 9803, Cell Signaling Technology). The lysis buffer is used to lyse cells under nondenaturing conditions An example of a quencher compound is the compound shown in FIG. 1B, which irreversibly binds to BTK.

Isolating the Drug Bound and Quencher Bound Receptor from the Cell Lysate Solution Immunocapture is a highly selective sample cleanup method that takes advantage of the unique immunoaffinity of the target protein and the capture agent (Stevenson, L., et. al., Bioanalysis 2013, 5, 2903-2918). Selecting the right capture antibody with high immunocapture efficiency for endogenous target is key for the success of the assay. One skilled in the art would know how to generate antibodies specific to their target protein should a specific antibody not be commercially available.

Figure 4:
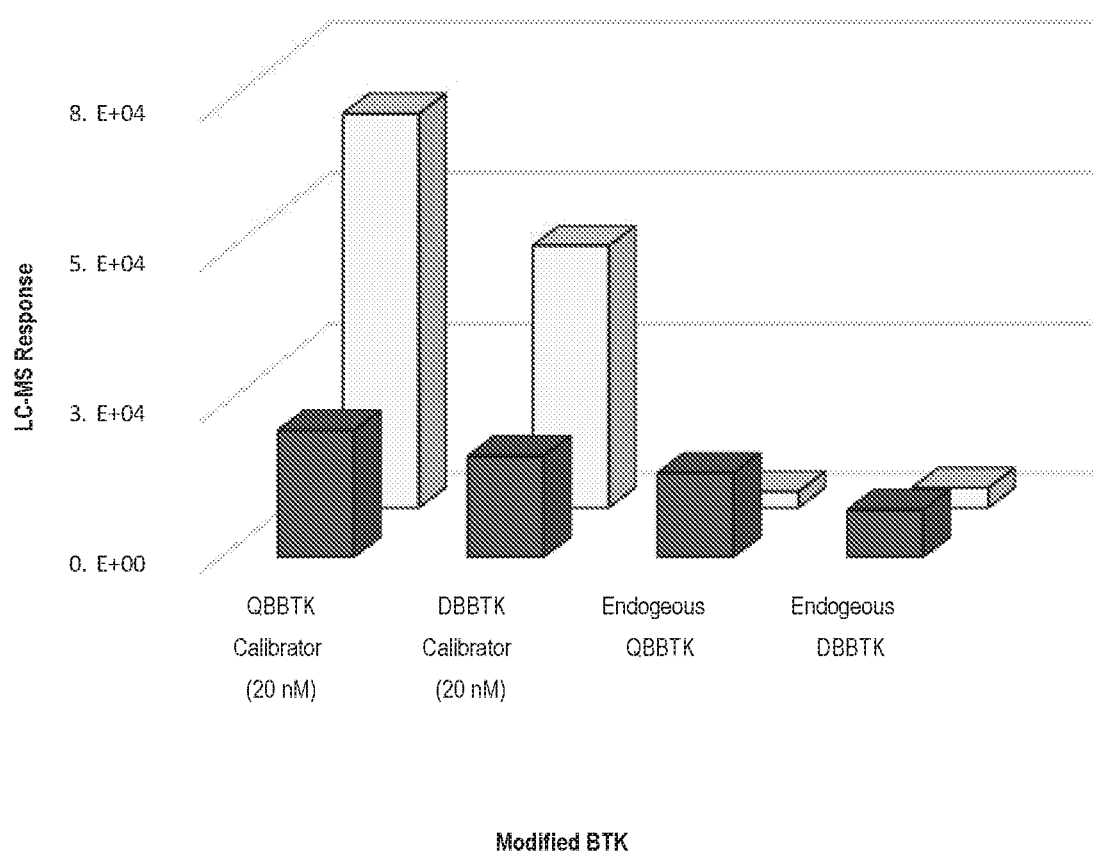
FIG. 4 shows that capture antibodies from different vendors (■mAb-D3H5, □mAb-MAB5807) have differential immunocapture performance between the endogenous BTK in human blood and recombinant BTK (used as the calibrators).
Figure 5A:
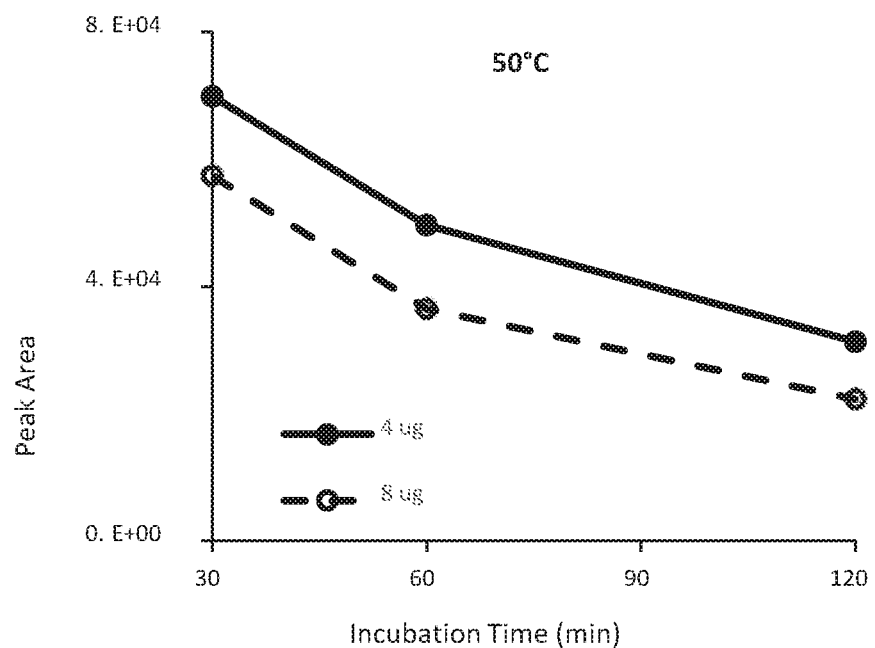
FIG. 5A-5D shows the effect of trypsin concentration, digestion time on LC-MS/MS responses of the surrogate peptides generated from DB-BTK (5A and 5B) and QB-BTK (5C and 5D) at 50° C. (5A and 5C) or 60° C. (5B and 5D). The surrogate peptides, DB-QRP or QB-QRP were measured by LC-HRMS on a Thermo's Q Exactive™ Hybrid Quadrupole-Orbitrap™ Mass Spectrometer. The experiments were conducted in triplicate for each condition.
Figure 5B:
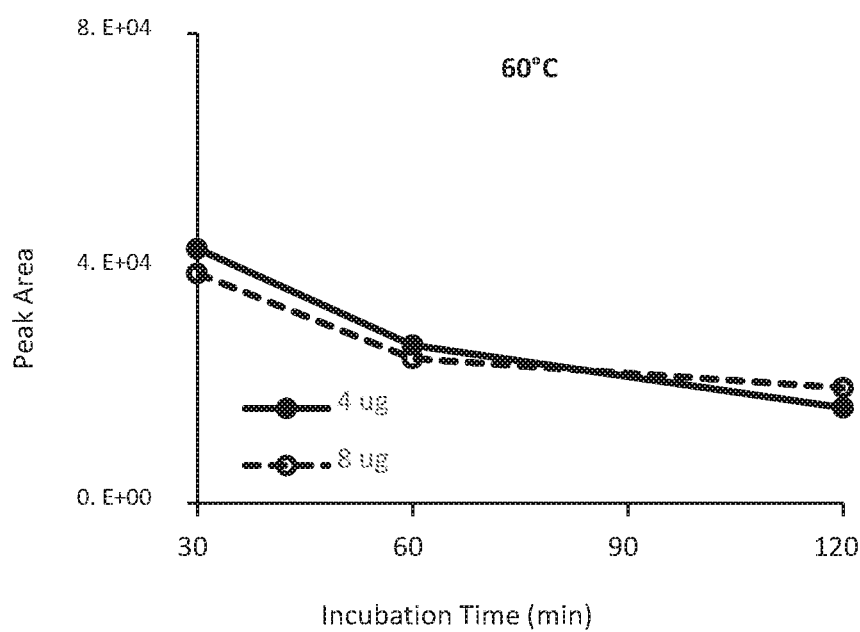
Figure 5C:
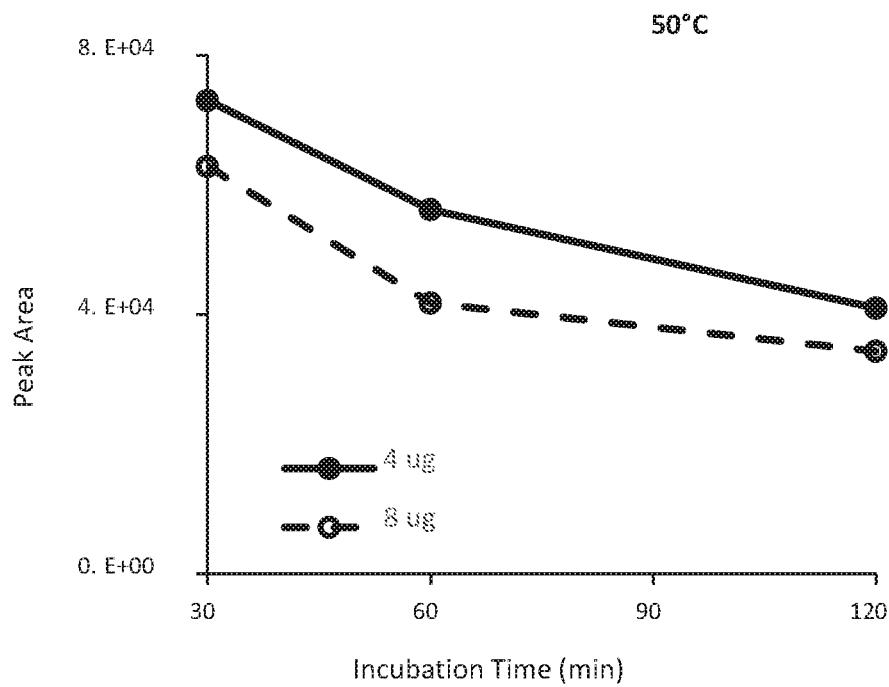
Figure 5D:
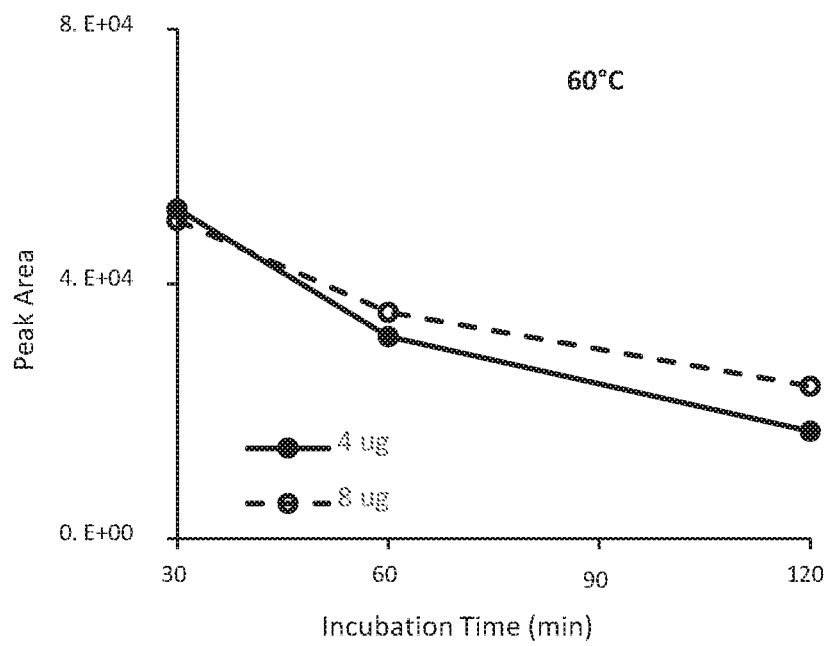

To evaluate the immunocapture efficiency antibodies are screened using drug bound and quencher bound target. Antibodies are selected based on high affinity to both the drug bound and quencher bound target. For example, to select antibodies specific for BTK, the immunocapture capability of commercially available mAb clone #MAB5807 and mAb clone #D3H5 were evaluated. Surprisingly, the mAb, clone #MAB5807 was unable to detect endogenous BTK, DB-BTK or QB-BTK at the needed sensitivity although it shows high affinity to recombinent BTK, DB-BTK or QB-BTK. As shown in FIG. 4, while the LC-MS response from the endogenous BTK was too low when using mAb clone #5807, the other clone, mAb clone #D3H5 gave a moderate response for drug bound and quencher bound recombinant BTK, and a greater response for both drug bound and quencher bound endogenous BTK. Since the ultimate goal was to determine the drug bound and quencher bound endogenous BTK in human blood, clone #D3H5 was selected for use in the BTK RO assay.

Generating Drug Bound and Quencher Bound Receptor Surrogate Peptides

The receptor surrogate peptides generated for use in the RO assay must contain the binding site of the compound of interest. Additionally, the surrogate peptides must be sensitive to LC-MS detection.

In one embodiment of the invention, the isolated drug bound and quencher bound receptor is digested with one or more proteases selected from the group consisting of serine proteases, cysteine proteases, threonine proteases, aspartic proteases, glutamic proteases and metalloproteases. Examples of acceptable proteases include trypsin, chymotrypsin, Glu-C protease, Lys-C protease, Lys-N protease, Asp-N protease, Arg-C protease.

Table 1 describes the surrogate peptides generated when BTK is digested with various proteases.

TABLE 1

BTK peptides generated when treated with various proteases

| Protease | BTK Peptide Generated | SEQ ID NO |
|---|---|---|
| Trypsin | QRPIFIITEYMANG CLLNYLR | 1 |
| Chymotrypsin | MANGCLLNY | 2 |
| Glu-C | YMANGCLLNYLRE | 3 |
| Lys-C | QRPIFIITEYMANG CLLNYLREMRHRFQ TQQLLEMCK | 4 |
| Lys-N | KQRPIFIITEYMAN GCLLNYLREMRHRF QTQQLLEMC | 5 |
| Asp-N | DEFIEEAKVMMNLS HEKLVQLYGVCTKQ RPIFIITEYMANGC LLNYLREMRHRFQT QQLLEMCK | 6 |
| Arg-C | GQYDVAIKMIKEGS MSEDEFIEEAKVMM NLSHEKLVQLYGVC TKQRPIFIITEYMA NGCLLNYLR | 7 |

Since the quantitation of the drug bound target and quencher bound target is based on the MS response of the representative surrogate peptides, the digestion yields of these surrogate peptides could have dramatic impact on the sensitivity of detection.

In one embodiment of the invention, the digestion step is performed before or after elution of the drug bound and quencher bound receptor from the immunocapture substrate. Preferably, the digestion step is performed while the target is bound to the immunocapture substrate. For example, the drug bound and quencher bound BTK was treated with a trypsin digestion while still bound by the immunocapture bead.

Measuring the Amount of Surrogate Peptides

In one embodiment of the invention, the receptor occupancy can be determined by measuring quencher bound and drug bound surrogate peptides simultaneously in a single LC-MS/MS run.

Figure 6:
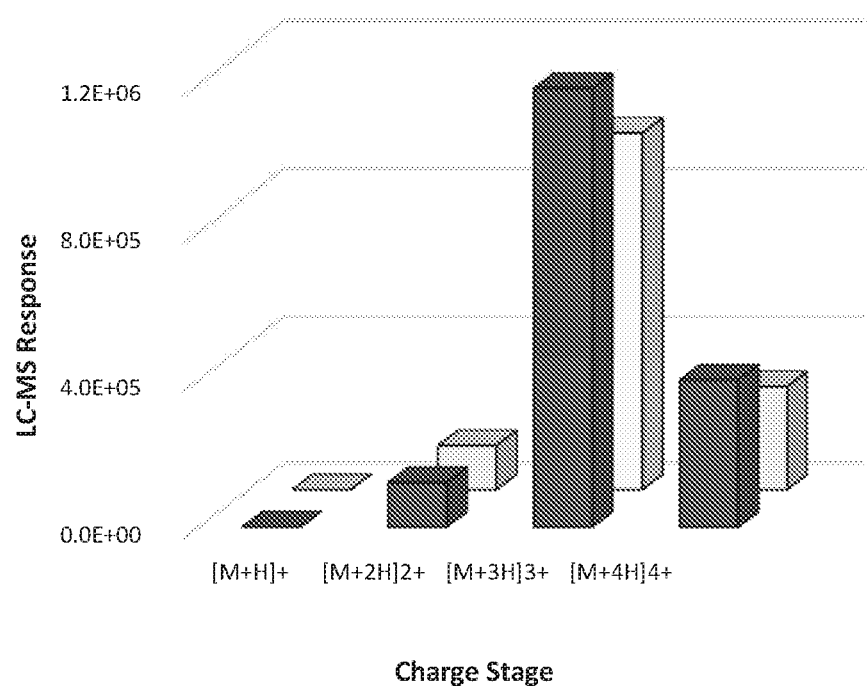
FIG. 6 shows a comparison of the signal response for each charge stage for both DB-BTK(■) and QB-BTK(□).
Figure 7A:
FIG. 7A-7C shows (7A) electrospray positive ion MS/MS product ion spectrum of $[M+3H]^{3+}$ at m/z 967.4 for DB-QRP peptide; (7B) electrospray positive ion MS/MS product ion spectrum of $[M+3H]^{3+}$ at m/z 962.5 for QB-QRP peptide; and (7C) electrospray positive ion MS/MS product ion spectrum of $[M+3H]^{3+}$ at m/z 965.9 for SIL-QB-QRP peptide (Internal Standard) obtained from a Sciex's Triple Quad 5500 mass spectrometer.
Figure 7B:
Figure 7C:
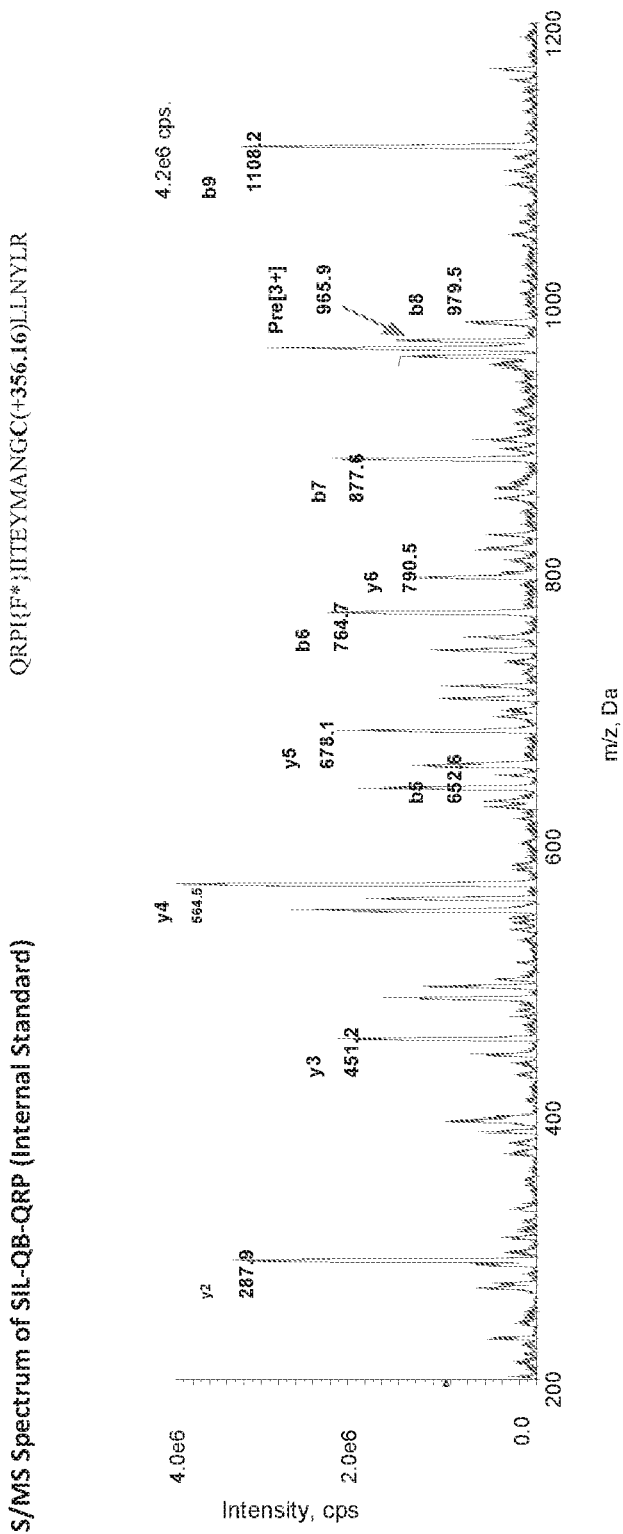

During initial method development, the DB-BTK and QB-BTK generated from the reaction was analyzed using a Q Exactive HF high resolution mass spectrometry (HRMS). By using the accurate mass expected from the surrogate peptides, all surrogate peptides were identified. The signal abundance of each charge stage is shown in FIG. 6. The data show that both DB-BTK and QB-BTK gave the highest response for the three charge stage, therefore, the $[M+3H]^{3+}$ ion was used for both DB-QRP (surrogate peptide of DB-BTK) and QB-QRP (surrogate peptide of QB-BTK) as the parent ion for MRM detection. As shown in FIG. 7A-7C, several product ions were shown in the MS/MS spectra. The product ion corresponding to $y_2$ ion (m/z ~288) and $b_6$ ion (m/z ~755 for DB-QRP and QB-QRP, m/z ~765 for IS) show good intensity for MRM detection with $y_2$ ion better than $b_6$ ion. Since $y_2$ ion at m/z ~288 has an interference peak shown in the MRM channels of DB-QRP and QB-QRP, $b_6$ ion was used as the product ion for MRM detection.

Figure 8A:
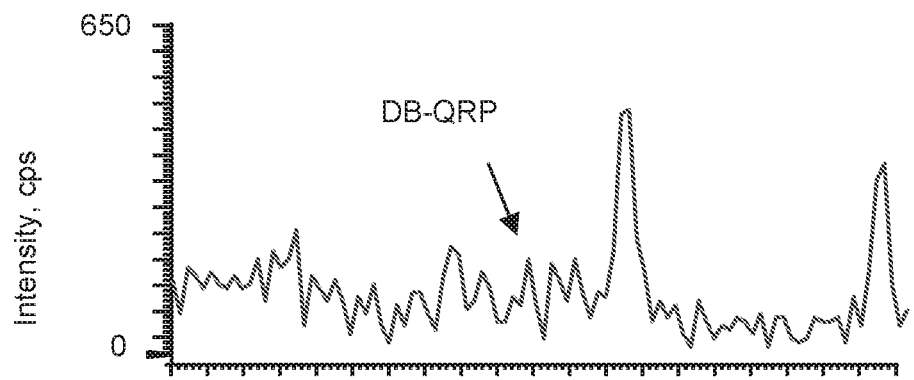
FIG. 8A-8F shows multiple reaction monitoring (MRM) chromatograms for DB-QRP (surrogate peptide for DB-BTK) (8A-8C) and QB-QRP (surrogate peptide for QB-BTK) (8D-8F), and their internal standards (IS); (8A and 8D) chromatograms of the analytes obtained from blank monkey blood lysate in which the contributions of endogenous BTK were eliminated by pre-treatment with the quencher or drug individually; (8B and 8E) chromatograms of the analytes obtained from monkey blood lysate containing the analyte at LLOQ and its IS; (8C and 8F) chromatograms of the IS obtained from monkey blood lysate only containing the IS. (c and f) $[^{13}C_9, ^{15}N]$-QB-QRP was used as the IS for DB-QRP and QB-QRP.
Figure 8B:
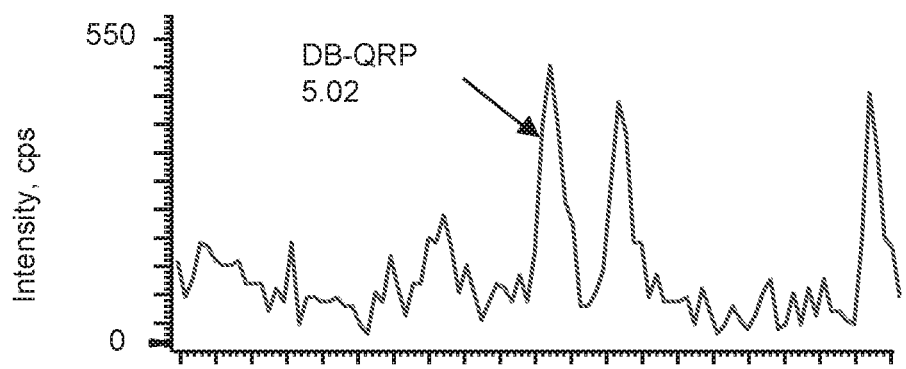
Figure 8C:
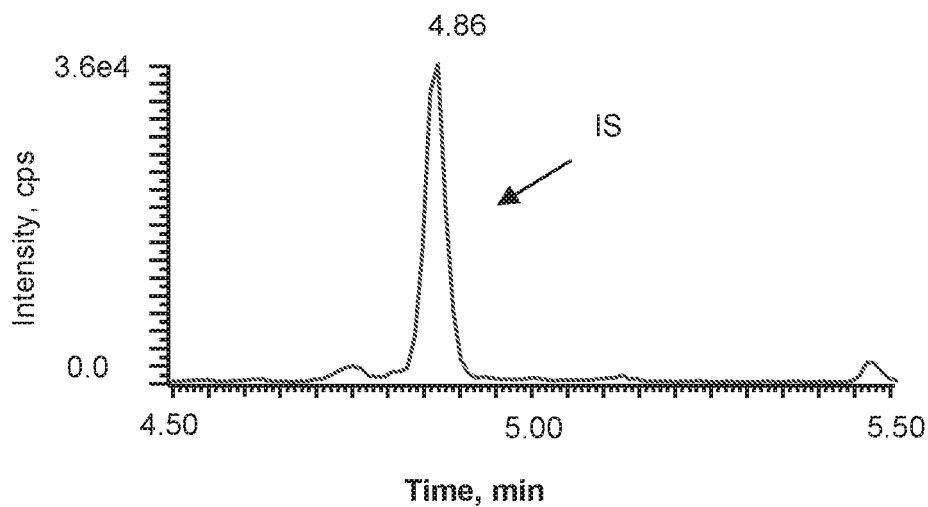
Figure 8D:
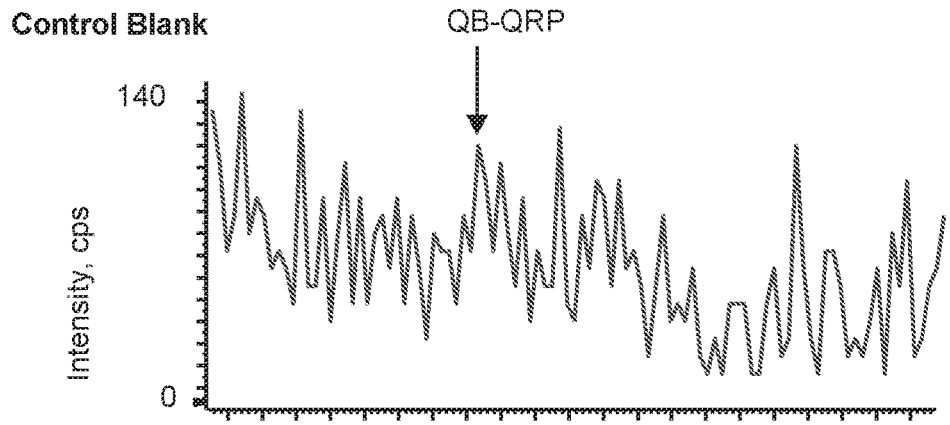
Figure 8E:
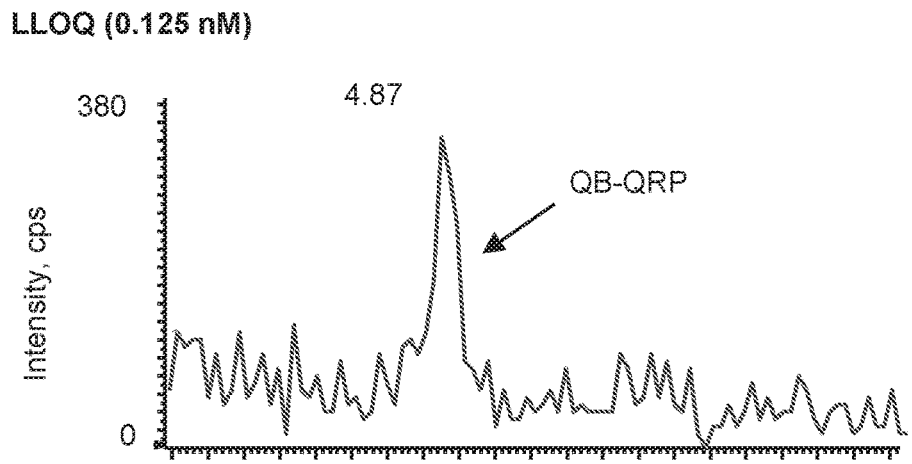
Figure 8F:
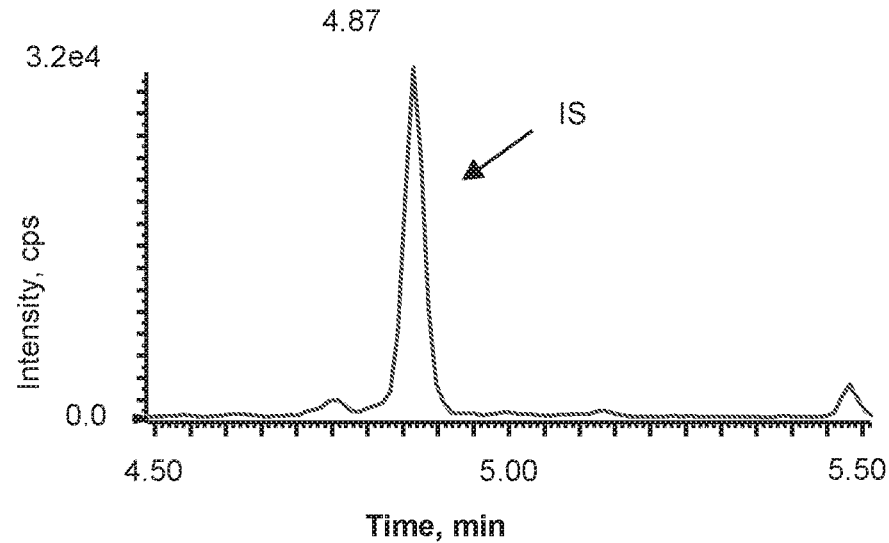
Figure 9A:
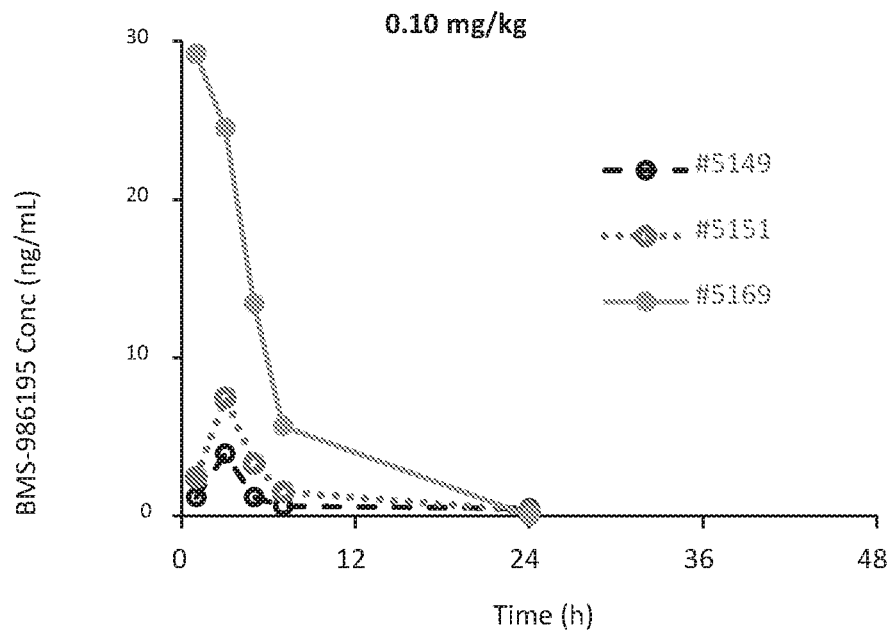
FIG. 9A-9D shows the PK and PD results obtained from monkeys #5149, #5151 and #5169 administered the compound (BMS-986195) shown in FIG. 1A at two different doses 0.10 mg/kg or 0.5 mg/kg. Blood samples were collected at 1, 3, 5, 7, and 24 h on Day 1 for PK evaluation (data shown in 9A and 9B) and collected at pre-dose, 1, 3, 5, 7, 24, 48, 72, 144 and 168 h for PD evaluation (data shown in 9C and 9D) (see Example 2).
Figure 9B:
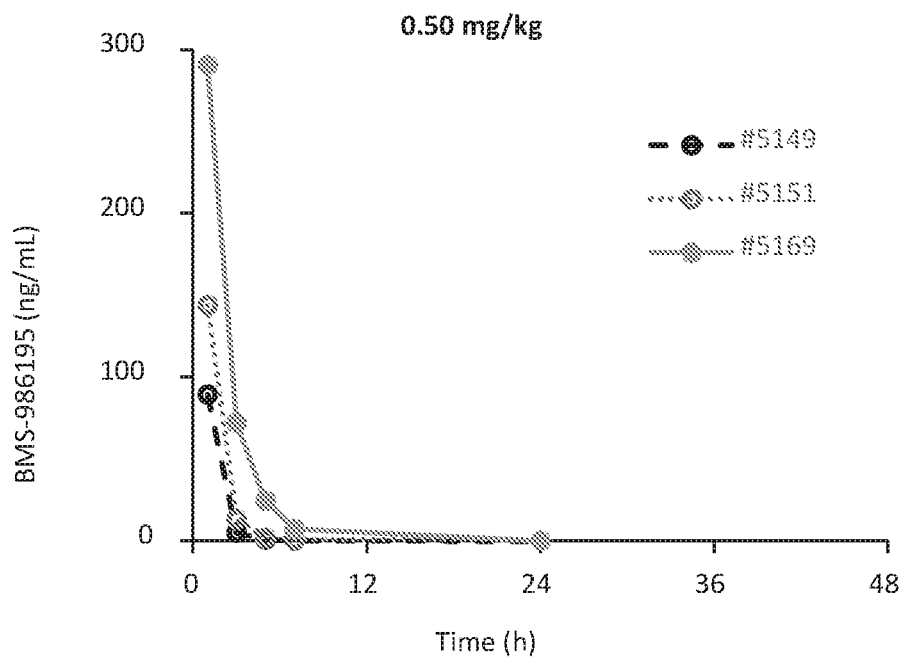
Figure 9C:
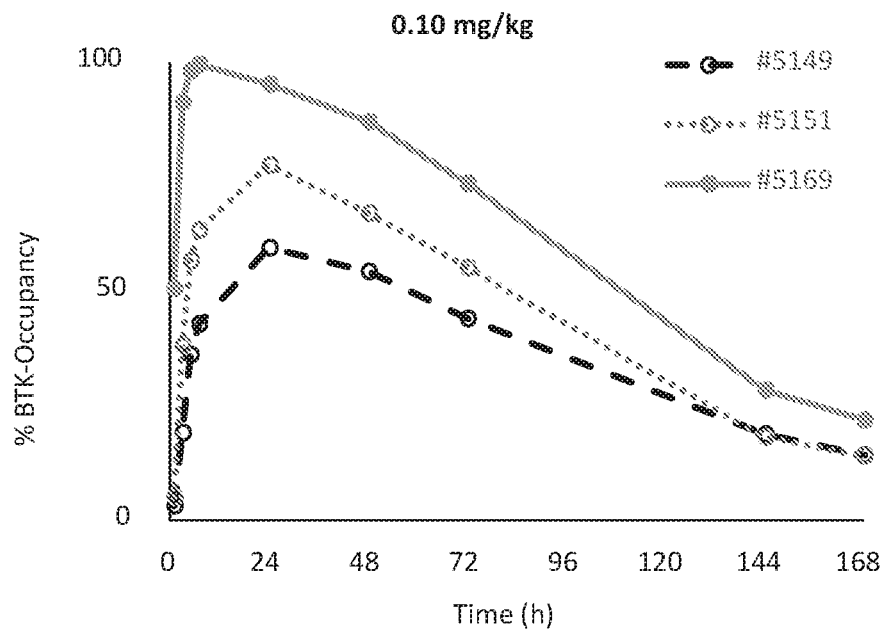
Figure 9D:
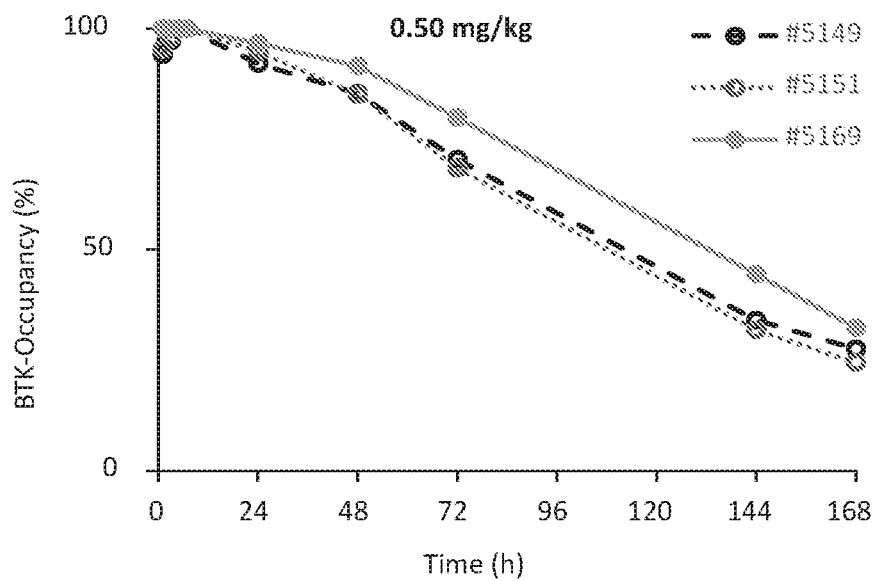

Typical MRM chromatograms of DB-QRP, QB-QRP and IS from blank monkey blood lysate, blank monkey blood lysate spiked with DB-BTK and QB-BTK at the concentration of the LLOQ at 0.250 nM for DB-BTK, and 0.125 nM for QB-BTK are shown in FIGS. 8a, 8b, 8d and 8e. Typical MRM mass chromatograms of $[^{13}C^9, ^{15}N]$-QB-QRP from blank monkey blood lysate with only IS is shown in FIGS. 8c and 8f. No significant interfering peaks from the blank monkey lysate were found at the retention time or in the ion channel of either DB-QRP, QB-QRP or the IS when control blank monkey blood lysate was analyzed. DB-QRP, QB-QRP, and their ISs were eluted from UHPLC column with retention of 5.02, 4.87 and 4.87 min, respectively.

Lower Limit of Quantitation

The lower limits of quantitation (LLOQ) for DB-QRP and QB-QRP were 0.250 nM and 0.125 nM, which are the lowest concentrations for both analytes in the standard curves. As shown in FIGS. 8b and 8e, the signal-to-noise (S/N) of DB-QRP or QB-QRP at the LLOQ concentration levels were at least 3 or higher.

Calibration Curve Linearity and Accuracy and Precision of QCs

For method qualification to quantify BTK RO in blood lysate, all standard curves were fitted to a 1/x weighted quadratic regression model with standard curves ranging from 0.250 to 12.5 nM for DB-BTK, and 0.125 to 12.5 nM for QB-BTK. In each run, for at least two-thirds of the calibration standards, the deviations of the back-calculated concentrations from their nominal values were within ±20.0% (±25.0% at the LLOQ level). As shown in Tables 2-3, the deviations of the back-calculated concentrations from their nominal values were within ±11.1% for DB-BTK, and within ±19.8% for QB-BTK for three accuracy and precision runs. The accuracy and precision was evaluated using the quality control samples.

TABLE 2

Data summary obtained from the precision and accuracy of the standard curve samples for DB-BTK assay

| | Runs | | | | | |
|---|---|---|---|---|---|---|
| | Run 1 | | Run 2 | | Run 3 | |
| Nominal Conc (nM) | Pred Conc | % Dev | Pred Conc | % Dev | Pred Conc | % Dev |
| 0.250 | 0.229 | −8.4 | 0.237 | −5.2 | 0.256 | 2.4 |
| 0.500 | 0.482 | −3.6 | 0.505 | 1.0 | 0.495 | −1.0 |

TABLE 2-continued

Data summary obtained from the precision and accuracy of the standard curve samples for DB-BTK assay

| | Runs | | | | | |
|---|---|---|---|---|---|---|
| | Run 1 | | Run 2 | | Run 3 | |
| Nominal Conc (nM) | Pred Conc | % Dev | Pred Conc | % Dev | Pred Conc | % Dev |
| 1.000 | 1.080 | 8.0 | 1.110 | 11.0 | 0.986 | −1.4 |
| 2.000 | 2.186 | 9.3 | 1.810 | −9.5 | 2.012 | 0.6 |
| 5.000 | 4.776 | −4.5 | 5.256 | 5.1 | 4.853 | −2.9 |
| 10.000 | 9.568 | −4.3 | 9.376 | −6.2 | 11.114 | 11.1 |
| 12.500 | 12.951 | 3.6 | 13.203 | 5.6 | 11.341 | −9.3 |

TABLE 3

Data summary obtained from the precision and accuracy of the standard curve samples for QB-BTK assay

| | Runs | | | | | |
|---|---|---|---|---|---|---|
| | Run 1 | | Run 2 | | Run 3 | |
| Nominal Conc (nM) | Pred Conc | % Dev | Pred Conc | Pred Conc | Pred Conc | % Dev |
| 0.125 | 0.126 | 0.8 | 0.13 | 4.0 | 0.116 | −7.2 |
| 0.250 | 0.217 | −13.2 | 0.264 | 5.6 | 0.209 | −16.4 |
| 0.500 | 0.544 | 8.8 | 0.442 | −11.6 | 0.599 | 19.8 |
| 1.000 | 0.996 | −0.4 | 0.991 | −0.9 | 1.058 | 5.8 |
| 2.000 | 2.142 | 7.1 | 2.076 | 3.8 | 2.023 | 1.2 |
| 5.000 | 4.963 | −0.7 | 4.846 | −3.1 | 4.807 | −3.9 |
| 10.000 | 9.282 | −7.2 | 10.5 | 5.0 | 9.835 | −1.7 |
| 12.500 | 13.159 | 5.3 | 12.116 | −3.1 | 12.757 | 2.1 |

TABLE 4

Assay qualification: quality control data obtained from monkey blood lysate containing 25, 50 and 90% BTK-occupancy

| | Run 1 | | | Run 2 | | | Run 3 | | |
|---|---|---|---|---|---|---|---|---|---|
| QC Level (n = 6) | DB-BTK (nM) | QB-BTK (nM) | % BTK RO | DB-BTK (nM) | QB-BTK (nM) | % BTK RO | DB-BTK (nM) | QB-BTK (nM) | % BTK RO |
| QC 25% BTK RO | 1.331 | 3.821 | 25.8 | 0.933 | 3.616 | 20.5 | 0.951 | 2.768 | 25.6 |
| | 1.371 | 3.918 | 25.9 | 1.102 | 3.835 | 22.3 | 0.817 | 2.743 | 22.9 |
| | 1.499 | 4.385 | 25.5 | 1.18 | 4.12 | 22.3 | 0.79 | 2.364 | 25.0 |
| | 1.408 | 3.85 | 26.8 | 0.882 | 3.727 | 19.1 | 0.804 | 2.219 | 26.6 |
| | 1.21 | 3.604 | 25.1 | 1.076 | 3.985 | 21.3 | 0.867 | 2.63 | 24.8 |
| | 1.214 | 3.653 | 24.9 | 0.933 | 3.687 | 20.2 | 0.781 | 2.353 | 24.9 |
| QC 50% BTK RO | 2.541 | 2.283 | 52.7 | 1.849 | 2.391 | 43.6 | 1.739 | 1.739 | 50.0 |
| | 2.629 | 2.454 | 51.7 | 2.105 | 2.403 | 46.7 | 1.85 | 1.648 | 52.9 |
| | 2.783 | 2.658 | 51.1 | 1.736 | 2.033 | 46.1 | 1.651 | 1.659 | 49.9 |
| | 2.479 | 2.456 | 50.2 | 2.166 | 2.52 | 46.2 | 1.553 | 1.596 | 49.3 |
| | 2.208 | 2.137 | 50.8 | 2.384 | 2.625 | 47.6 | 1.827 | 1.667 | 52.3 |
| | 2.813 | 2.424 | 53.7 | 2.301 | 2.500 | 47.9 | 1.577 | 1.485 | 51.5 |
| QC 90% BTK RO | 5.035 | 0.449 | 91.8 | 4.299 | 0.471 | 90.1 | 3.234 | 0.35 | 90.2 |
| | 4.830 | 0.384 | 92.6 | 4.600 | 0.495 | 90.3 | 2.684 | 0.237 | 91.9 |
| | 4.881 | 0.427 | 92.0 | 3.652 | 0.436 | 89.3 | 2.933 | 0.274 | 91.5 |
| | 4.080 | 0.356 | 92.0 | 4.677 | 0.495 | 90.4 | 3.139 | 0.286 | 91.6 |
| | 4.631 | 0.419 | 91.7 | 5.009 | 0.511 | 90.7 | 3.235 | 0.296 | 91.6 |
| | 4.485 | 0.420 | 91.4 | 4.710 | 0.505 | 90.3 | 2.866 | 0.279 | 91.1 |

As shown in Table 4, the difference between the measured % BTK RO and the theoretical % BTK RO were within ±5% for all QCs for all three runs except for one out of six QC_25% RO samples and one out of six QC_50% RO samples in run 2 that had a difference between measured and theoretical values of >5%.

The % CV and % Dev were within 10% for all QCs in all three runs except for one QC_25% RO, with a % Dev of −16.2% (Table 5). The results demonstrated that the method was accurate and precise for the analysis of % BTK RO in monkey blood lysate.

TABLE 5

Quality control data summary obtained from monkey blood lysate containing 25, 50 and 90% BTK-occupancy (n = 6).

| BTK RO QCs (Nom Value, %) | DB-BTK (nM) | QB-BTK (nM) | Measured Mean BTK RO (%) | CV % | % Dev |
|---|---|---|---|---|---|
| Run 1 | | | | | |
| QC_25% RO | 1.339 ± 0.113 | 3.872 ± 0.279 | 25.7 | 2.6 | 2.7 |
| QC_50% RO | 2.576 ± 0.223 | 2.402 ± 0.177 | 51.7 | 2.5 | 3.4 |
| QC_90% RO | 4.657 ± 0.342 | 0.409 ± 0.033 | 91.9 | 0.4 | 2.1 |
| Run 2 | | | | | |
| QC_25% RO | 1.018 ± 0.118 | 3.828 ± 0.192 | 21.0 | 6.0 | −16.2 |
| QC_50% RO | 2.090 ± 0.253 | 2.412 ± 0.204 | 46.4 | 3.3 | −7.3 |
| QC_90% RO | 4.491 ± 0.470 | 0.486 ± 0.028 | 90.2 | 0.5 | 0.2 |
| Run 3 | | | | | |
| QC_25% RO | 0.835 ± 0.064 | 2.513 ± 0.231 | 25.0 | 4.8 | −0.1 |
| QC_50% RO | 1.700 ± 0.126 | 1.632 ± 0.086 | 51.0 | 2.9 | 2.0 |
| QC_90% RO | 3.015 ± 0.224 | 0.287 ± 0.037 | 91.3 | 0.6 | 1.5 |

Stability Evaluation

The established stabilities for DB-BTK and QB-BTK in monkey blood lysate are summarized in Table 6. The results indicated that the stability of DB-BTK and QB-BTK had no or minimal impact on the % BTK RO as the difference between the measured % BTK RO and the theoretical % BTK RO were within ±5% for all QCs regardless of the absolute concentration of DB-BTK or QB-BTK decreasing after 2 freeze-thaw cycles at −80° C. or stored at RT for 24 h or stored at −80° C. for 224 days.

TABLE 6

Stability evaluation of the quality control samples at % BTK RO of 25% and 90%

| Stability Evaluation | Measured DB-BTK (nM) | Measured QB-BTK (nM) | Mean Measured BTK RO (%) | CV (%) | Dev (%) |
|---|---|---|---|---|---|
| 2 Freeze-Thaw Cycles | | | | | |
| QC_25% RO | 0.968 ± 0.108 | 3.435 ± 0.307 | 22.0 | 3.0 | −12.2 |
| QC_90% RO | 4.372 ± 0.157 | 0.505 ± 0.050 | 89.7 | 0.9 | −0.4 |
| 24 h at RT | | | | | |
| QC_25% RO | 0.912 ± 0.086 | 3.099 ± 0.177 | 22.8 | 6.9 | −9 |
| QC_90% RO | 3.019 ± 0.120 | 0.398 ± 0.040 | 88.4 | 1.0 | −1.8 |
| 224 Days at −80° C. | | | | | |
| QC_25% RO | 0.890 ± 0.067 | 2.500 ± 0.186 | 26.3 | 4.4 | 5.1 |
| QC_90% RO | 3.719 ± 0.039 | 0.367 ± 0.032 | 91.0 | 0.8 | 1.1 |

Use of Immunocapture LC-MS/MS Receptor Occupancy Assay

The measurement of RO is a critical determination for relating efficacy to mechanism in preclinical animal models and in clinical studies. In practice, RO is particularly useful in making dose escalation decisions in the first in human (FIH) study.

Example 1

Figure 1B:
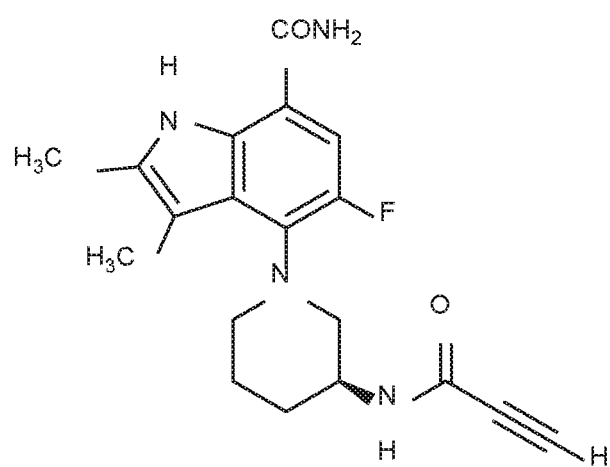
Figure 3:
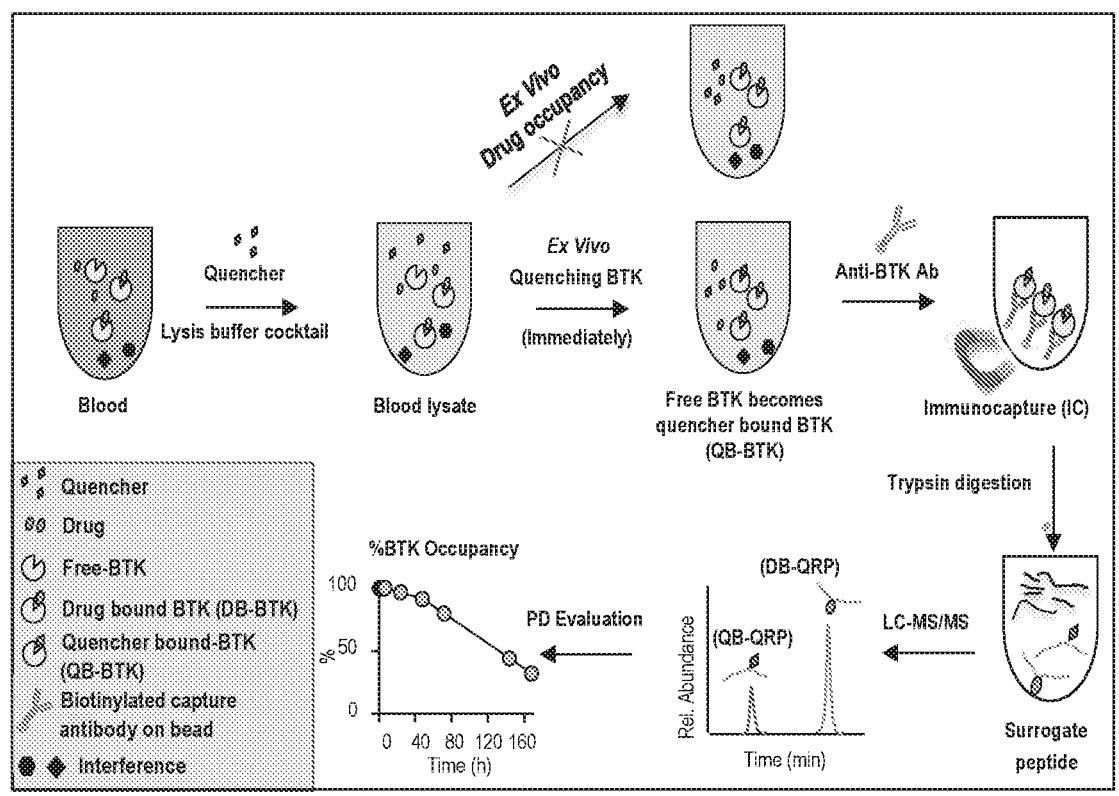
FIG. 3 shows a schematic representation of BTK RO assay by immunocapture-LC-MS/MS. Surrogate peptides used are drug bound peptide (DB-QRP) and quencher bound peptide (QB-QRP).

Preparation of Drug Bound BTK (DB-BTK) and Quencher Bound BTK (QB-BTK) Standards and Quality Control Samples
Reagents and Materials The drug and quencher compounds shown in FIGS. 1A and 1B, respectively, were synthesized by Research & Development at Bristol-Myers Squibb (Princeton, NJ). The biotinylated rabbit anti-BTK monoclonal antibody (Lot No: D3H5, Cat No: 12624) and 10× lysis buffer (Cat No: 9803) were purchased from Cell Signaling Technology (Danvers, MA). Dynabeads Myone streptavidin T1 beads (Cat No: 65602) was purchased from ThermoFisher Scientific (Carlsbad, CA). The recombinant BTK protein (Cat No: PV3587) was purchased from Life Technologies (Carlsbad, CA). The protease inhibitor (Cat No: 539134) was purchased from Millipore Sigma (Billerica, MA). The internal standard (IS) used for the assay, [$^{13}C_9$, $^{15}N$]-QB-QRP containing flanking amino acids in both N and C terminus (Table 8), was synthesized by the Department of Chemical Synthesis at Bristol-Myers Squibb (BMS) (Princeton, NJ, USA). Monkey ACD-A whole blood was purchased from Bioreclamation Inc. (Westbury, NY). All other reagents were of analytical grade. The MagnaBot 96 Magnetic Separation Device (Cat No: V8151) was purchased from Promega Corporation (Madison, WI).

Preparation of the Reference Standards for Drug Bound BTK (DB-BTK)

Recombinant BTK (5.9 µM, 200 µL) was combined with 400 µL of PBS, and then spiked with 15 µL of 1.0 mg/mL drug solution (compound shown in FIG. 1A) in acetonitrile (2701 µM drug, 15 µL). The solution was then incubated at RT for 1 h, resulting in a DB-BTK concentration of 1919 nM. DB-BTK concentration was based on the total free BTK amount used for the reaction because the conversion of free BTK to DB-BTK was ~100% in the presence of excess amount of drug.

Preparation of the Reference Standards for Quencher Bound BTK (QB-BTK)

Recombinant BTK (5.9 µM, 200 µL) was combined with 400 µL of PBS, and then spiked with 15 µL of 1.0 mg/mL quencher solution (compound shown in FIG. 1B) in acetonitrile (2806 µM quencher, 15 µL). The solution was incubated at RT for 1 h, resulting in a QB-BTK concentration of 1919 nM. QB-BTK concentration was based on the total free BTK amount used for the reaction because the conversion of free BTK to QB-BTK was ~100% in the presence of excess amount of quencher.

Preparation of Lysis Buffer Cocktail Containing Quencher: 2× Lysis Buffer with 0.0133× Protease Inhibitor and 1.5 µM of Quencher Solution:

One vial containing 15 mL of 10× lysis buffer was mixed with 1.0 mL of protease inhibitor and 80 µL of 0.5 mg/mL quencher solution (compound shown in FIG. 1B) in DMSO. The solution was then diluted with 59 mL of deionized water for a total volume of 75 mL.

Preparation of Lysis Buffer Cocktail Containing Drug: 2× Lysis Buffer with 0.0133× Protease Inhibitor and 1.5 µM of Drug Solution One vial containing 15 mL of 10× lysis buffer was mixed with 1.0 mL of protease inhibitor and 83 µL of 0.5 mg/mL drug solution (compound shown in FIG. 1A) in DMSO. The solution was then diluted with 59 mL of deionized water for a total volume of 75 mL.

Preparation of Lysate+433 (100% QB-BTK) from Monkey Blood

Monkey ACD-A whole blood (3.5 mL) was combined with 7 mL of the lysis buffer containing 1.5 µM of quencher (compound shown in FIG. 1B). The samples were shaken for 1 hour at room temperature.

Preparation of Lysate+195 (100% DB-BTK) from Monkey Blood

Monkey ACD-A whole blood (3.5 mL) was combined with 7 mL of the lysis buffer containing 1.5 µM of drug (compound shown in FIG. 1A). The samples shaken for 1 hour at room temperature.

Preparation of Quality Control Samples (QCs) Using Blood Lysate Containing Endogenous BTK The BTK RO QCs are prepared by mixing different percentages of the Lysate+433 and Lysate+195. Lower QC (LQC), Middle QC (MQC) and High QC (HQC) with % BTK RO at 25%, 50% and 90% were prepared by mixing Lysate+433/Lysate+195 at 2250/750, 1500/1500, 300/2700 (v/v), respectively as shown in Table 7.

TABLE 7

Preparation of Quality Control Samples Using Monkey Blood Lysate Containing Endogenous BTK

| BTK RO QCs | Theoretical BTK Occupancy (%) | Lysate + 433[a] (µL) | Lysate + 195[b] (µL) | Total Volume (µL) |
|---|---|---|---|---|
| QC_25% RO | 25 | 2250 | 750 | 3000 |
| QC_50% RO | 50 | 1500 | 1500 | 3000 |
| QC_90% RO | 90 | 300 | 2700 | 3000 |

[a]Lysate + 433 was obtained by pretreatment of monkey lysate with quencher solution (FIG. 1B).
[b]Lysate + 195 was obtained by pretreatment of monkey lysate with drug solution (FIG. 1A).

Preparation of DB-BTK (BTK+195) Standard Curve: Use the Monkey Blood Lysate+433

Calibration standards (STDs) at 0.250, 0.500, 1.00, 2.00, 5.00, 10.0 and 12.5 nM of DB-BTK were prepared in monkey blood lysate containing 0% DB-BTK by independent dilution of the DB-BTK stock solutions (1919 nM in buffer). During preparation, intermediate dilutions of 200 and 20 nM for DB-BTK were prepared by diluting 1919 nM of DB-BTK stock solution with Blood Lystae+433, and then further diluted to the final STD samples. The nominal concentrations was based on the blood volume, the actual concentration in blood lysate were ⅓ of each due to dilution factor of 3.

Preparation of QB-BTK (BTK+433) Standard Curve: Use the Monkey Blood Lysste+195

Calibration standards (STDs) at 0.125, 0.250, 0.500, 1.00, 2.00, 5.00, 10.0 and 12.5 nM of QB-BTK were prepared in monkey blood lysate containing 0% QB-BTK by independent dilution of the QB-BTK stock solutions (1919 nM in buffer). During preparation, intermediate dilutions of 200 and 20 nM for QB-BTK were prepared by diluting 1919 nM of QB-BTK stock solution with Blood Lystae+195, and then further diluted to the final STD samples. The nominal concentrations was based on the blood volume, the actual concentration in blood lysate were ⅓ of each due to dilution factor of 3.

Preparation of Streptavidin T1 Capture Beads with Anti-BTK Biotinylated Antibody. The concentration of Dyna-beads Myone streptavidin T1 beads for immunoprecipitation was 10 mg/mL. The binding capacity for biotinylated mAb was 20 µg mAb/mg bead. A total of 25 mL of streptavidin T1 beads were aliquoted into 10 tubes of 2.5 mL in each. The samples were washed with 3 mL of PBST solution. DynaMag™-5 magnet was used to separate the magnetic beads from liquid sample matrices. After discarding the last wash, the beads were re-suspended in 2.5 mL of PBST in each tube, then 0.500 mL of biotinylated anti-BTK antibody (1 mg/mL, Lot No: D3H5) was added. The samples in 10 tubes (0.500 mL) were incubated at RT for 1 h. The beads were separated from the solution, and the beads in each tube were washed with 3 mL of PBST. The beads in the tubes were re-suspended in 2.5 mL of PBST. The final anti-BTK antibody concentration was 0.2 µg/µL beads. The samples were stored at 4° C. for future use.

Immunocapture for drug bound BTK (DB-BTK) and quencher bound BTK (QB-BTK) Enrichment from Blood Lysate. Aliquots of 3000 µL blood lysate samples for control monkey blood lysate, calibration standards, quality control samples or monkey study samples were centrifuged at room temperature. Anti-BTK capture antibody (60 µL at 0.2 µg mAb/µL bead) on beads was added to the supernatant of the centrifuged samples, the samples were incubated at RT for 120 minutes followed by centrifugation. The supernatant was removed and PBST was added to the bead samples. The samples were transferred into a LowBind 96-well plate on a TECAN liquid handler and placed on top of the MagnaBot 96 Magnetic separation device. The beads were washed with 800 µL of PBST twice, followed by 500 µL of 25 mM NH$_4$OAc with 0.05% Tween-20. After removing the washing buffer, the beads in the LowBind 96-well well plate were used for trypsin digestion as described below.

Trypsin Digestion. After the addition of IS (100 µL of 0.5 µg/mL SIL-QB-QRP in 25 mM NH$_4$OAc with 0.05% Tween-20) except for blank lysate (to which 100 µL of 25 mM NH$_4$OAc with 0.05% Tween-20 was added) into the beads in 96-well plate, 25 µL of 100 mM NH$_4$HCO$_3$ was added to each sample. The samples were digested by addition of 25 µL of freshly prepared trypsin solution at 160 ng/µL in 100 mM NH$_4$HCO$_3$, and incubated at 50° C. for 30 min before quenching with 20 µL of 50%/50% MeOH/formic acid (v/v). The samples were briefly vortexed and then put on top of a MagnaBot 96 device, the supernatant was transferred to a new 96-well plate, followed by a centrifugation at 4000 rpm for 2 minutes. The samples were analyzed by LC-MS/MS.

UHPLC-MS/MS Analysis. For assay qualification and sample analysis, an AB Sciex Triple Quad 5500 mass spectrometer from Sciex (Forster City, CA) was used for LC-MS/MS data acquisition.

The following LC-MS/MS condition was used for assay qualification and PD sample analysis. For each processed sample, a 50 µL volume of the digest was injected into an ultra-high performance liquid chromatography (UHPLC) system (model LC-30AD, Shimadzu Scientific Instruments, Inc., Columbia, MD). The UHPLC-MS/MS conditions described below were used specifically for the quantitation of occupied and quenched BTK in monkey blood lysate. A Waters CORTECS™ UPLC C18+ column (2.1×100 mm, 1.6 µm, Waters Corporation, Milford, MA) was used for the analysis of the DB-QRP and QB-QRP peptide. Mobile phase A was composed of 0.1% formic acid in water; while mobile phase B was 0.1% formic acid in acetonitrile. The UHPLC separation was performed using a gradient elution starting with 15% B and keeping for 0.5 min, followed by changing % B from 15% to 30% in 2.5 min, and then changing % B from 30% to 45% in 4.9 min, then increasing % B from 45% to 90% in 0.1 min and keeping for 1 min, then decreasing % B from 95% to 15% in 0.1 min, keeping for 1.0 min, and stopping at 10.0 min. The flow-rate was 0.600 mL/min and the column temperature was 60° C. With a switching-valve configuration, the UHPLC eluent was introduced with a time window of 3.0-6.5 min into a Triple Quad 5500™ mass spectrometer equipped with a turbo ion spray source obtained from AB Sciex (Forster City, CA). The mass spectrometer was operated in positive electrospray ionization mode with the following settings: curtain gas, 30 units; CAD gas, 9 units; gas 1, 65 units; gas 2, 65 units; turbo ion spray voltage of positive 4000 V and turbo probe temperature at 600° C. The mass spectrometer was operated in MRM mode with the transition of m/z 962.493>755.40, 967.174>755.40, and 965.825>765.50 for QB-QRP, DB-QRP and the SIL-QB-QRP (IS), respectively (Table 8). The raw data was processed using Analyst® software (version 1.6.2, AB SCIEX) for chromatographic peak integration and processed results were exported to Watson LIMS™ (version 7.4, ThermoFisher Scientific Inc.) for regression of calibration standards and concentration calculations of QCs and other samples. Statistical data regarding assay performance (ANOVA) was calculated using Watson LIMS™.

TABLE 8

MRM Transitions used for LC-MS/MS detection for surrogate peptides and their stable isotope labeled internal standards.

| Surrogate Peptide | Surrogate Peptide Sequences | $[M + 3H]^{3+}$ | MRM Transition |
|---|---|---|---|
| DB-QRP$^a$ (AA# 467-487) | 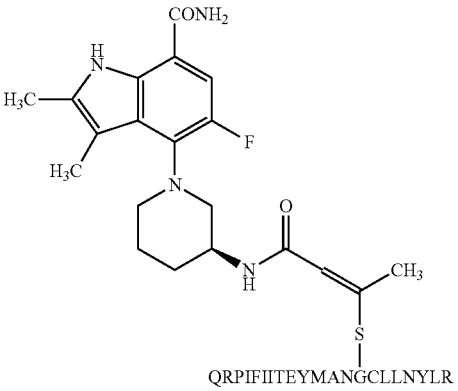 Formula: $C_{135}H_{205}FN_{34}O_{32}S_2$ | 966.8368 | m/z 967.17→755.4 |
| QB-QRP$^a$ (AA# 467-487) | 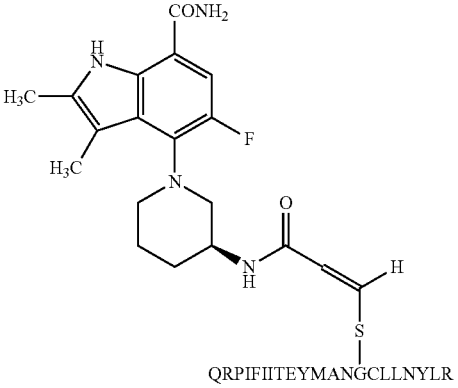 Formula: $C_{134}H_{203}FN_{34}O_{32}S_2$ | 962.1649 | m/z 962.50→755.4 |

TABLE 8-continued

MRM Transitions used for LC-MS/MS detection for surrogate peptides and their stable isotope labeled internal standards.

| Surrogate Peptide | Surrogate Peptide Sequences | MRM [M + 3H]$^{3+}$ | Transition |
|---|---|---|---|
| [$^{13}C_9,^{15}N$]-QB-QRP[b] (Internal Standard) | 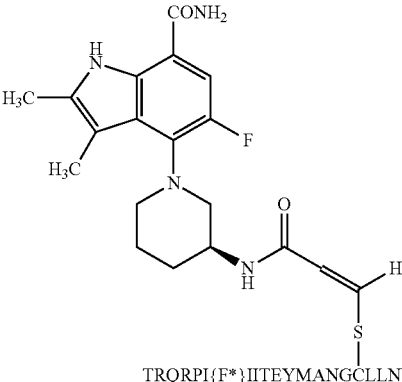 TRQRPI{F*}IITEYMANGCLLNYLREA Formula after trypsin digestion: $^{13}C_9C_{125}H_{203}F^{15}NN_{33}O_{32}S_2$ | 965.5073 | m/z 965.83→765.5 |

[a]The surrogate peptide is named as QRP based on the first three amino acid symbols of 21 amino acids in the tryptic peptide. DB-QRP = Drug bound QRP peptide; QB-QRP = Quencher bound QRP peptide.
[b]The symbol of F* represents a [$^{13}C_9,^{15}N$]-phenylalanine. The peptide segment with underlines was tryptic peptide and monitored in LC-MS/MS assay.

Assay Qualification. The assay qualification consisted of three accuracy and precision runs with additional stability evaluation including freeze-thaw, RT and long term stability of the BTK RO QCs. The linearity of the method was assessed using seven DB-BTK (0.250 nM-12.5 nM) or eight QB-BTK (0.125 nM-12.5 nM) calibration curve points in all qualification runs. A quadratic regression model with 1/x weighing was used for quantitation. The acceptance criteria was the following: in each run, for at least two-thirds of the calibration standards, the deviations of the back-calculated concentrations from their nominal values were within ±20.0% (±25.0% at the LLOQ level). For BTK RO QCs, for at least 50% of the QCs at each level, the difference between the measured % BTK RO and the theoretical % BTK RO should be within ±5%. For example, for BTK RO QC_25%, the measured % BTK RO should be within 25.0±5.0%. The assay selectivity was assessed using blank blood lysate only, QC0 (blank lysate with IS only).

Example 2

Application to Monkey PD Studies.

To assess the utility and robustness of the BTK RO assay by LC-MS/MS in comparison to an established ELISA based assay, a single ascending dose study of compound shown in FIG. 1A was performed. Cynomologus Monkeys were administered drug compound 1A at 0.1, 0.2 and 0.5 mg/kg PO. Blood samples were collected at 1, 3, 5, 7, and 24 h on Day 1 for PK evaluation and collected at pre-dose, 1, 3, 5, 7, 24, 48, 72, 144 and 168 h for PD evaluation using BTK RO assays by LC-MS/MS as well as ligand binding assay (LBA) described in Example 3.

PD Samples for BTK RO Assay by LC-MS/MS.

Before PD sample collection, the following lysis buffer cocktail containing 2× lysis buffer with 0.0133× protease inhibitor and 1.5 μM of quencher (compound shown in FIG. 1B) solution was prepared: One vial containing 15 mL of 10× lysis buffer was mixed with 1.0 mL of protease inhibitor and 80 μL of 0.5 mg/mL quencher compound 1B in DMSO. The solution was then diluted with 59 mL of deionized water for a total volume of 75 mL.

As mentioned above, 2 mL of blood samples were collected at the set time point. 1.5 mL of the collected blood was lysed with 3-mL of the lysis buffer cocktail containing quencher compound 1B. Immediately after mixing, the samples were shaken for 1 hour at room temperature. The blood lysate samples were stored at or below −70° C. immediately after the collection. The samples were used for immunocapture with LC-MS/MS assay.

Example 3

BTK RO Assay by LBA

Monkey ACD-A treated whole blood was collected at set time points after dosing and added to a 96-well, V-bottom, 2 ml plate (Costar, cat #3960) and lysed with 2× lysis buffer (Cell Signaling, cat #9803) containing protease inhibitor (Calbiochem, cat #539134) and biotinylated probe (BMT-105186). The lysate was transferred to a streptavidin-coated plate (ThermoFisher Scientific, neutrAvidin® cat #15128) and incubated with shaking for 1 hour at room temperature. After washing, anti-BTK antibody (Cell Signaling, cat #8547, 1:1000 dilution in PBS+0.05% Tween20+0.5% BSA) was added and incubated while shaking for 1 hour at room temperature. The plate was washed, followed by addition of goat anti-rabbit horseradish peroxidase secondary antibody (Invitrogen, G21234) at a 1:2,500 dilution in PBS+0.05% Tween20+0.5% BSA. The ELISA was developed with the addition of tetramethyl benzidine (TMB) (Sigma, cat #T0440) and allowed to develop and stopped with addition of 2.0 N sulfuric acid. The absorbance at 450 nm was read and the relative % of BTK inactivation of study samples was calculated from a standard curve of samples containing different ratios of lysates from normal monkey blood mixed with quenched lysates from blood pretreated with 2 μM BMT-126867 to allow for complete BTK inactivation prior to lysis.

Pharmacokinetic Analysis by LC-MS

A 0.5 mL of monkey blood was collected at the set time points for PK evaluation. Each blood sample was centrifuged to separate plasma. 10 μL of the 125 μM quencher solution (compound shown in FIG. 1B) was immediately added to 200 μL of plasma. After mixing, the samples were stored at −20° C. and used for LC-MS/MS analysis.

What is claimed is:

1. An assay method for determining receptor occupancy, said method comprising the steps of:
   a) collecting a blood sample from a subject treated with a drug of interest that irreversibly binds a receptor,
   b) adding a lysis solution containing a quencher to the blood sample,
   c) isolating the receptor,
   d) digesting the isolated receptor to generate surrogate peptides,
   e) measuring an amount of a drug bound surrogate peptide and a quencher bound surrogate peptide and determining drug receptor occupancy by comparing the amount of drug bound surrogate peptide to the total amount of drug bound and quencher bound surrogate peptides.

2. An assay method for determining drug receptor occupancy in a subject dosed with a drug of interest that covalently binds to a receptor, said method comprising the steps of:
   a) collecting a blood sample from subject treated with the drug of interest
   b) adding a lysis solution comprising a quencher that irreversibly binds at the same receptor site as the drug of interest to the blood sample,
   c) isolating drug bound and quencher bound receptor by immunocapture,
   d) digesting the isolated drug bound and quencher bound receptor to generate drug bound and quencher bound surrogate peptides,
   e) measuring an amount of a drug bound surrogate peptide and a quencher bound surrogate peptide using Liquid chromatography-tandem mass spectrometry (LC-MS/MS) and determining the amount of receptor bound to drug by comparing the amount of drug bound surrogate peptide to the total amount of drug bound and quencher bound surrogate peptides.

3. The assay of claim 2, wherein the drug of interest is Compound A:

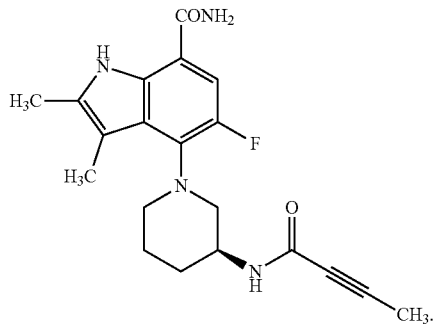

Compound A

4. The assay of claim 2, wherein the quencher of step (b) is Quencher Compound:

Quencher Compound

[Structure: indole with CONH2, H3C, H3C, F substituents and piperidine-propynamide with terminal H]

5. The assay of claim 1, wherein digestion step (d) is trypsin digestion.

6. The assay of claim 1, wherein the amount of surrogate peptides is measured by LC-MS/MS.

7. A method for determining Bruton's tyrosine kinase (BTK) receptor occupancy in a subject dosed with a drug, wherein the drug is Compound A:

Compound A

[Structure of Compound A]

said method comprising the steps of:
a) collecting a blood sample from the subject dosed with the drug,
   adding a lysis solution containing a quencher to the blood sample, wherein the quencher is Quencher Compound:

Quencher Compound

[Structure of Quencher Compound]

b) isolating drug bound and quencher bound BTK with anti-BTK biotinylated antibody bound to Streptavidin T1 Beads, c) digesting the isolated drug bound and quencher bound BTK-antibody complex with trypsin to generate surrogate peptides, d) measuring an amount of a drug bound surrogate peptide and a quencher bound surrogate peptide using Liquid chromatography-tandem mass spectrometry (LC-MS/MS) and determining the amount of BTK bound to drug by comparing the amount of drug bound surrogate peptide to the total amount of drug bound and quencher bound surrogate peptides.

8. The assay of claim 1, wherein the drug of interest is Compound A:

Compound A

[Structure of Compound A]

9. The assay of claim 1, wherein the quencher of step (b) is Quencher Compound:

Quencher Compound

[Structure of Quencher Compound]

10. The assay of claim 2, wherein digestion step (d) is trypsin digestion.

11. The assay of claim 1, wherein the quencher binds the receptor at the same site as the drug of interest.

12. The assay of claim 1, wherein the quencher covalently binds the receptor.

13. The assay of claim 7, wherein Quencher Compound binds BTK at the same site as Compound A.

14. The assay of claim 7, wherein Quencher Compound covalently binds BTK.

15. The assay of claim 1, wherein the drug of interest covalently binds the receptor.

16. The assay of claim 2, wherein the drug of interest covalently binds the receptor.

17. The assay of claim 7, wherein the Compound A covalently binds BTK.

* * * * *